(12) United States Patent
Oakley et al.

(10) Patent No.: US 8,930,218 B1
(45) Date of Patent: *Jan. 6, 2015

(54) SYSTEMS AND METHODS FOR BUILDING MEDICAL DIAGNOSTIC APPARATUS USING A DIGITAL LIBRARY

(75) Inventors: David Oakley, Boulder, CO (US);
Michael Hickey, Boulder, CO (US)

(73) Assignee: WAVi, Boulder, CO (US)

( * ) Notice: Subject to any disclaimer, the term of this patent is extended or adjusted under 35 U.S.C. 154(b) by 451 days.

This patent is subject to a terminal disclaimer.

(21) Appl. No.: 12/505,185

(22) Filed: Jul. 17, 2009

Related U.S. Application Data

(60) Provisional application No. 61/082,008, filed on Jul. 18, 2008, provisional application No. 61/082,015, filed on Jul. 18, 2008.

(51) Int. Cl.
*G06Q 50/24* (2012.01)

(52) U.S. Cl.
USPC .............................................................. 705/3

(58) Field of Classification Search
USPC ...................................................... 705/2, 3
See application file for complete search history.

(56) References Cited

U.S. PATENT DOCUMENTS

| | | | |
|---|---|---|---|
| 5,038,782 A | 8/1991 | Gevins et al. | |
| 5,479,934 A | 1/1996 | Imran | |
| 6,167,298 A | 12/2000 | Levin | |
| 6,195,576 B1 | 2/2001 | John | |
| 6,381,481 B1 | 4/2002 | Levendowski et al. | |
| 6,912,414 B2 | 6/2005 | Tong | |
| 7,447,643 B1 | 11/2008 | Olson et al. | |
| 2002/0188216 A1 | 12/2002 | Kayyali et al. | |
| 2003/0023183 A1 | 1/2003 | Williams | |
| 2003/0232396 A1 | 12/2003 | Mathew et al. | |
| 2003/0233250 A1 | 12/2003 | Joffe et al. | |
| 2009/0088619 A1 | 4/2009 | Turner et al. | |
| 2009/0150183 A1 | 6/2009 | Schmitt et al. | |
| 2009/0182242 A1 | 7/2009 | Moses et al. | |
| 2010/0010831 A1* | 1/2010 | Fueyo et al. ...................... | 705/3 |

FOREIGN PATENT DOCUMENTS

| | | |
|---|---|---|
| WO | WO-0051028 A1 | 8/2000 |
| WO | WO-2009079377 A2 | 6/2009 |

OTHER PUBLICATIONS

International Search Report dated Jul. 7, 2011, in related Application No. PCT/US2010/049840, 5 pages.
In the US Patent and Trademark Office U.S. Appl. No. 12/567,249 Final Office Action dated Mar. 23, 2012, 10 pages.

(Continued)

*Primary Examiner* — John Pauls
(74) *Attorney, Agent, or Firm* — Squire Patton Boggs (US) LLP

(57) ABSTRACT

The medical data analysis system automatically identifies medical information sources which correlate to anomalies identified in a set of patient medical data relating to an identified patient. The system includes a digital library for providing access to a plurality of information sources which relate to interpreting patient medical data and possible diseases associated with the patient medical data. A data characterization module calculates normative variations of a set of patient medical data to identify anomalies. Based upon this statistical analysis, a digital library interface module searches the digital library for information sources relating to the set of patient medical data and interpretations of the identified anomalies. There is also an information access module which provides an authorized user, such as a physician, with access to the information sources returned by the digital library interface module and relating to this set of patient medical data.

22 Claims, 32 Drawing Sheets

(56) References Cited

OTHER PUBLICATIONS

In the US Patent and Trademark Office U.S. Appl. No. 12/567,249 Non-Final Office Action dated Nov. 7, 2011, 7 pages.
In the US Patent and Trademark Office U.S. Appl. No. 12/889,682 Non-Final Office Action dated Apr. 25, 2012, 8 pages.
In the US Patent and Trademark Office U.S. Appl. No. 12/889,697 Non-Final Office Action dated Feb. 28, 2012, 10 pages.
Casillas, Andrea; Third-Party Submission of Patents or Publications Under Peer Review Pilot Program, Sep. 2, 2011, 2 pages.
In the US Patent and Trademark Office U.S. Appl. No. 12/889,655 Non-Final Office Action dated Aug. 31, 2012, 9 pages.
In the US Patent and Trademark Office U.S. Appl. No. 12/889,682 Final Office Action dated Aug. 22, 2012, 7 pages.
In the US Patent and Trademark Office U.S. Appl. No. 12/889,697 Final Office Action dated Jul. 5, 2012, 11 pages.
In the US Patent and Trademark Office U.S. Appl. No. 12/567,249 Final Office Action dated Mar. 19, 2013, 9 pages.
In the US Patent and Trademark Office U.S. Appl. No. 12/567,249 Non-Final Office Action dated Nov. 7, 2012, 9 pages.
In the US Patent and Trademark Office U.S. Appl. No. 12/889,655 Final Office Action dated Dec. 13, 2012, 9 pages.

* cited by examiner

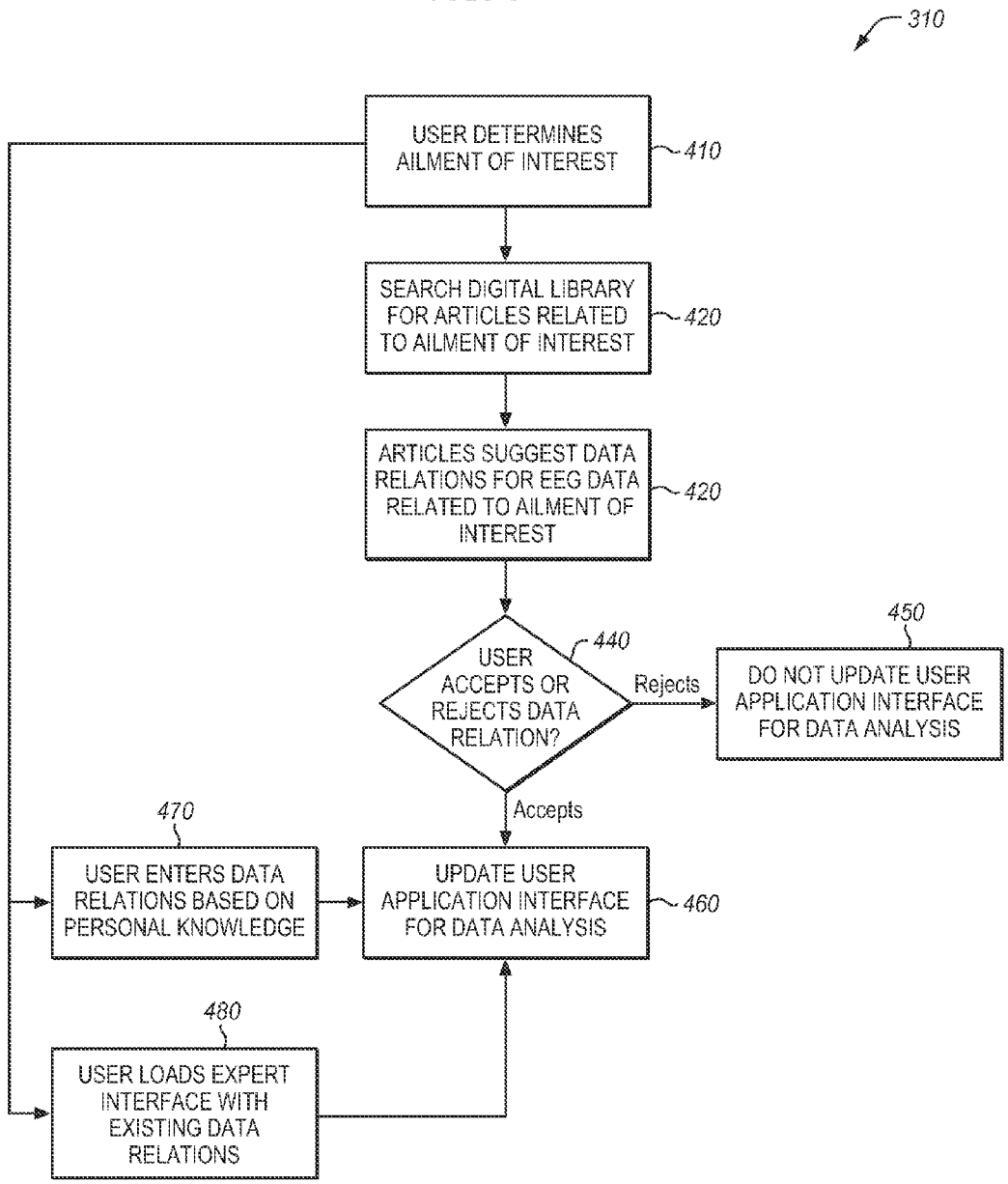

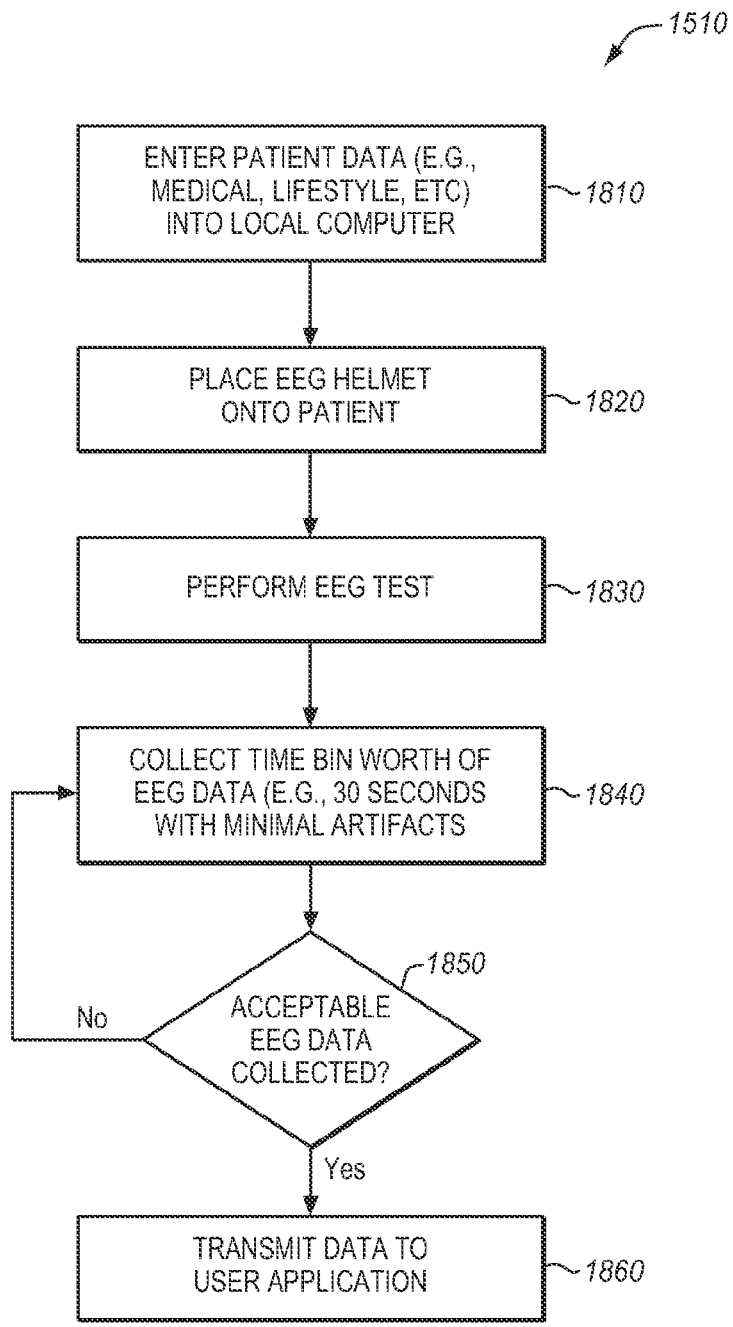

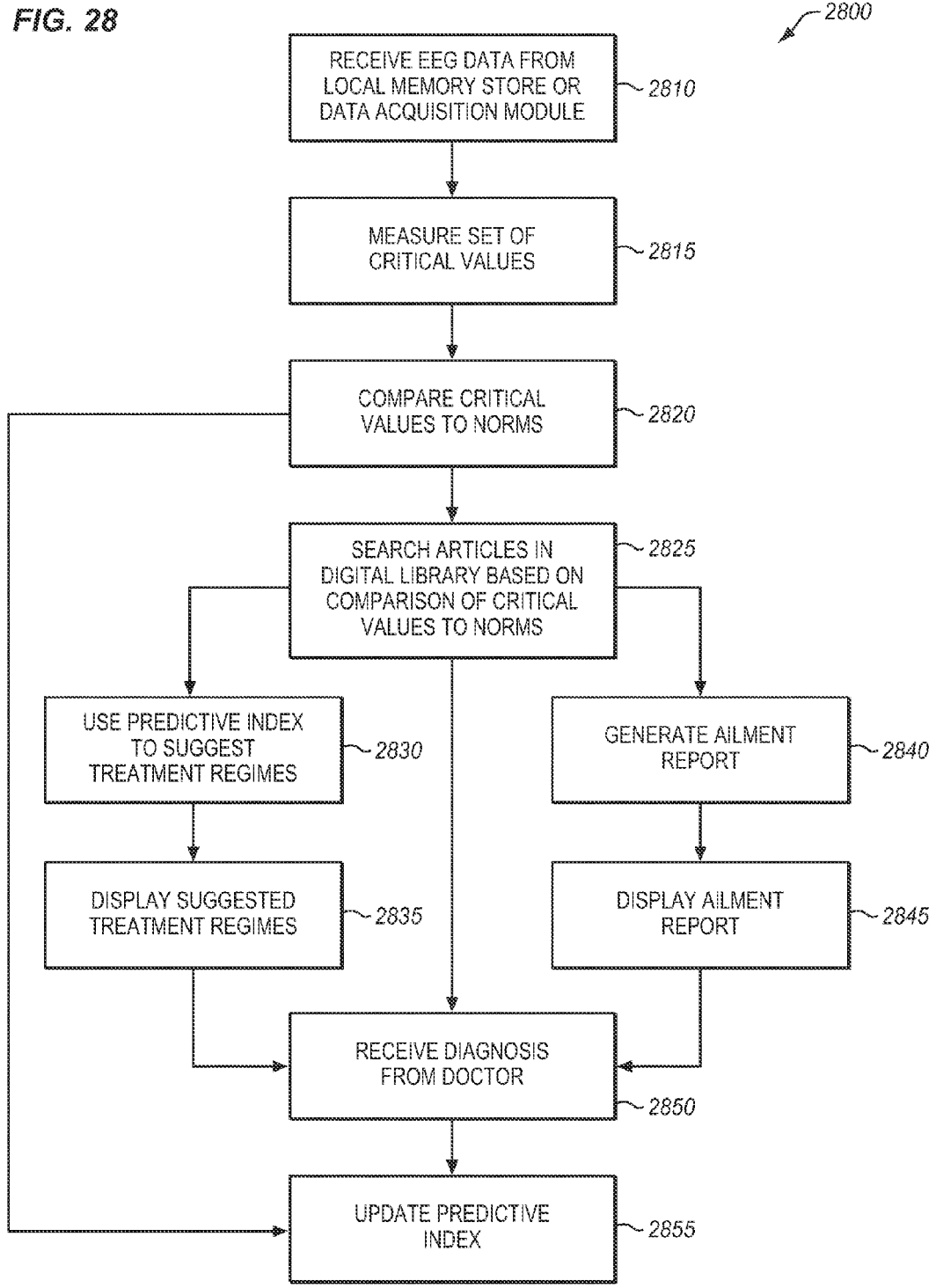

US 8,930,218 B1

SYSTEMS AND METHODS FOR BUILDING MEDICAL DIAGNOSTIC APPARATUS USING A DIGITAL LIBRARY

CROSS-REFERENCE TO RELATED APPLICATIONS

This Application claims the benefit of U.S. Provisional Application No. 61/082,008 filed on Jul. 18, 2008 and U.S. Provisional Application No. 61/082,015 filed on Jul. 18, 2008.

BACKGROUND OF THE INVENTION

Embodiments of the present invention generally relate to systems and methods for the statistical interpretation of complex data sets. More specifically, embodiments relate to the interpretation of brainwave signals by providing a user access to a digital library explaining possible interpretations of EEG data.

BRIEF SUMMARY OF THE INVENTION

According to various embodiments, systems and methods for interpreting medical data, such as EEG data, are provided that help a doctor interpret the medical data and provide an improved diagnosis of existing and/or future ailments. In some cases, the system for helping a user, e.g., a doctor, collect and interpret the medical data includes a data collection station, a data acquisition module, a user application station, one or more statistical databases, and a digital library.

In some embodiments of the present invention, the system includes a medical device, a digital library, a statistical characterization module, a digital library interface module, and a display module. The medical device can be a single medical device or combination of medical devices which are operable to collect medical data (e.g., physical data, psychological data, and the like) from a patient. Examples of medical devices include, but are not limited to, electro-encephalogram (EEG) systems, medical imaging systems, blood testing systems, heart rate monitors, and the like. According to various embodiments of the present invention, the medical device can be controlled through a data acquisition module or through the normal medical device interface.

BRIEF DESCRIPTION OF THE DRAWINGS

FIG. 4 is a flow chart illustrating operations 310 for setting up or updating a user application interface which may be used in accordance with some embodiments of the present invention;

FIG. 18 is a flow chart illustrating a set of operations 1510 for gathering EEG data in accordance with one or more embodiments of the present invention;

FIG. 28 is a flow chart with an example of a set of operations 2800 to update a predictive index 240 in accordance with some embodiments of the present invention;

DETAILED DESCRIPTION OF THE INVENTION

Figure 1A:
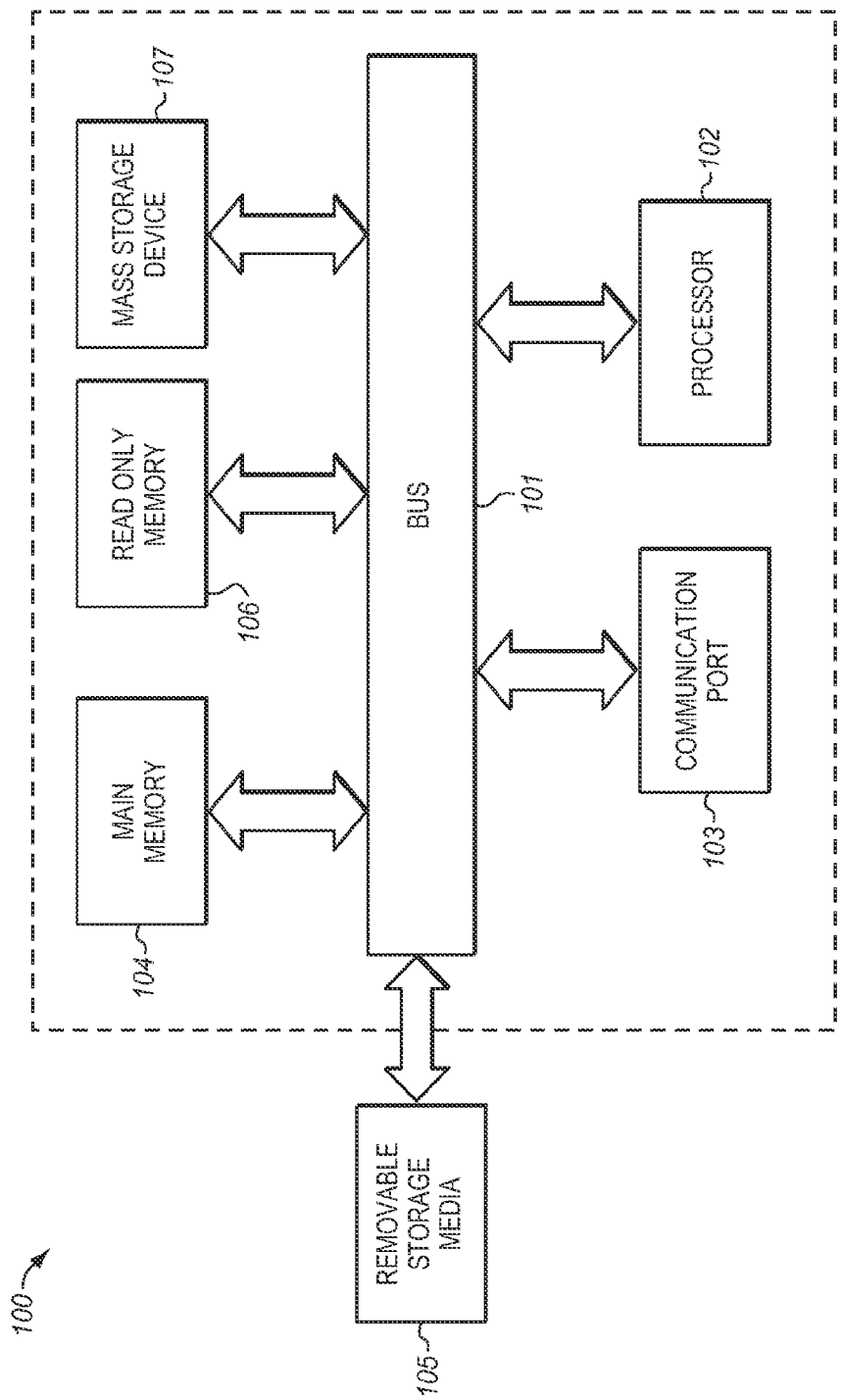
FIG. 1A illustrates an exemplary computer system 100, representing an exemplary server or client system, with which various features of the present invention may be utilized.

Systems and methods for the statistical interpretation of complex data sets are described. In particular, various embodiments of the present invention relate to systems and methods for providing interpretation of brainwave signals by supplying a user access to a digital library explaining possible interpretations of EEG data.

Embodiments of the present invention enhance the user's ability to interpret EEG data and provide an improved diagnosis of existing and/or future ailments. In some cases, the system for helping a user interpret EEG data includes a data collection station, a data acquisition module, a user application station, one or more statistical databases (e.g., normative, correlative, etc), and a digital library.

In some embodiments, the user application station and/or the data acquisition module are configured to collect and process raw EEG data. The raw EEG data can be collected and processed in real-time in conjunction with EEG tests of the patient. In other cases, the raw EEG data may be loaded from a memory store and processed. In either case, once the data is present, the raw EEG data can be adjusted by using reference placement values (to standardize the data between different helmets), filtered to remove noise interference, and transformed to frequency values (e.g., using FFTs or other digital signal processing algorithms). This data then can be accessed by the user application station to generate a statistical analysis to aid the doctor in assessing the patient's current and/or future wellness.

Embodiments of the user application station allow the clinician to customize displays of EEG data (e.g., spectral, topographical, raw data, etc.), to view only EEG data of interest (e.g., only beta waves from selected channels), and to compare patient EEG data to a demographic-matched (e.g., age) reference normative database using statistical analysis techniques. A request to process the EEG data is sent to an analysis platform which generates the statistical comparison.

The digital library used in accordance with embodiments of the present invention contains digitized information vehicles such as books, scientific research, manuscripts, videos, audio files, etc. that provide for interpretations of complex data sets (e.g., EEG data). The digital library can also include one or more of a trait scale index, a diagnostic index, a treatment index, and/or a predictive index that can aid a user of the system in explaining possible interpretations of EEG data and making improved diagnoses. These indexes contain various data relations that when statistically compared to a base group of normal subjects have been shown to indicate a particular psychological or physiological ailment or condition.

According to various embodiments, some of the digitized information vehicles include particular data relations which when used in comparing a patient's EEG to a base group of normal subjects have been shown to indicate a particular psychological or physiological ailment or condition. In some embodiments, the digitized information vehicles have an associated data link that can automatically populate the data relations selected by the user into the user application station for statistical comparison.

In using the analysis systems, one or more ailments of interest are selected. For example, when a patient arrives at a doctor's office, the doctor can make an initial assessment of the patient and determine that the patient may have a certain ailment (e.g., depression). In other situations, the doctor could have decided that he wants to screen all his patients for a certain ailment (e.g., attention deficit disorder). Upon deciding ailment(s) of interest, the doctor can set up the user application, or load a pre-existing interface setup, to determine if the EEG data is indicative of the ailment of interest. To do this, the doctor can use his personal knowledge about EEG data to setup data relations to be compared to the normal group. The doctor can also access the digital library and search for the ailment of interest (e.g., depression) and can search for articles which provide data relations that when used in comparing a patient's EEG to a base group of normal subjects has been shown to indicate the ailment. In other embodiments, the doctor can load pre-designed data relations that have been developed by experts in the field.

In addition to setting up desired data relations, patient data is loaded into the user application interface manually or through accessing an electronic medical record. Examples of the types of patient information that may be entered include, but are not limited to, stored EEG data, medical history, lifestyle information, answers to patient questionnaires, current and/or past medications, demographic information, and the like. The patient information is later used by the analysis system in selecting a base group for statistical comparison, generating predictive reports, and/or determining the efficacy of treatment.

The clinician then initiates an EEG test. The EEG data resulting from the test is either saved for later analysis and/or is directly transferred to the user application station. The pre-set data relations are evaluated using the current patient's EEG data. The data relations, patient information, and EEG data then are transmitted to a remote analysis platform. At the remote analysis platform, a base group is selected from the normative database based on the received patient information. For example, if the patient is a twenty-seven year old female, a base group may be selected from the normative database which includes normal EEG data from females with ages ranging from twenty-five to twenty-nine.

Once data for the base group has been collected, the desired data relations then are evaluated for each of the data sets and a Gaussian distribution for each data relation is formed from the base group EEG data. In some embodiments, Gaussian distributions of various data relations are stored directly in the normative database in order to reduce the computational time needed. Once the base group is determined and the Gaussian distributions of various data relations are accessed or computed, the patient data is compared to the base group.

In some embodiments, differences of the patient data relations from the normal EEG activity of the base group are expressed in the form of a z-score for each frequency band. Some embodiments provide for the percentile ranking, or standard score, of the patient's EEG data as it relates to the performance of normal individuals on one or more psychometric tests. However, as will be appreciated by one of ordinary skill in the art, various other statistical methods may be used to compare the patient EEG data with that of the base group. The results of the statistical analysis then are transferred back to the user application station to assist the user in diagnosis.

The results of the statistical analysis can be used in conjunction with statistical analysis of the patient EEG data with correlative databases, predictive databases, and trait indexes to determine the likelihood that the patient has, or will develop, a particular ailment. These results can be presented to the user, in some embodiments, through the user application by links to generated reports, quick reference color-coded scales, and/or other display formats.

In the following description, numerous specific details are set forth in order to provide a thorough understanding of embodiments of the present invention. It will be apparent, however, to one skilled in the art that embodiments of the present invention may be practiced without some of these specific details. In other instances, well-known structures and devices are shown in block diagram form.

Embodiments of the present invention include various steps that may be performed by hardware components or may be embodied in machine-executable instructions. The machine-executable instructions may be used to cause a general-purpose or special-purpose processor programmed with the instructions to perform the steps. Alternatively, the steps may be performed by a combination of hardware, software, and/or firmware.

Embodiments of the present invention may be provided as a computer program product, which may include a machine-readable medium having stored thereon instructions, which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

While, for convenience, embodiments of the present invention are described with reference to a statistical analysis to interpret EEG data, other embodiments of the present invention are equally applicable to various other operational models including, but not limited to, the interpretation of other medical data sets. Moreover, the statistical analysis platform described herein may be integrated with or form part of a system relating to statistical analysis of medical data. Alternatively, the statistical analysis platform tools may be accessed by users using a software package which may be directly installed on an end user's computer and used to interact with the remote statistical analysis platform.

An exemplary computer system 100, representing an exemplary server or client system, with which various features of the present invention may be utilized, will now be described with reference to FIG. 1A. In this simplified example, the computer system 100 comprises a bus 101 or other communication means for communicating data and control information, and one or more processors 102, such as Intel® Itanium® or Itanium 2 processors, coupled with bus 101.

Computer system 100 further comprises a random access memory (RAM) or other dynamic storage device (referred to as main memory 104), coupled to bus 101 for storing information and instructions to be executed by processor(s) 102. Main memory 104 also may be used for storing temporary variables or other intermediate information during execution of instructions by processor(s) 102.

Computer system 100 also comprises a read-only memory (ROM) 106 and/or other static storage device coupled to bus 101 for storing static information and instructions for processor(s) 102.

A mass storage device 107, such as a magnetic disk or optical disc and its corresponding drive, may also be coupled to bus 101 for storing information and instructions.

One or more communication ports 103 may also be coupled to bus 101 for supporting network connections and communication of information to/from the computer system 100 by way of a Local Area Network (LAN), Wide Area Network (WAN), the Internet, or the public switched telephone network (PSTN), for example. The communication ports 103 may include various combinations of well-known interfaces, such as one or more modems to provide dial up capability, one or more 10/100 Ethernet ports, one or more Gigabit Ethernet ports (fiber and/or copper), or other well-known network interfaces commonly used in current or future Internet work environments. In any event, in this manner, the computer system 100 may be coupled to a number of other network devices, clients, and/or servers via a conventional network infrastructure, such as an enterprise's Intranet and/or the Internet, for example.

Optionally, operator and administrative interfaces (not shown), such as a display, keyboard, and a cursor control device, may also be coupled to bus 101 to support direct operator interaction with computer system 100. Other operator and administrative interfaces can be provided through network connections connected through communication ports 103.

Finally, removable storage media 105, such as one or more external or removable hard drives, tapes, floppy disks, magneto-optical discs, compact disk-read-only memories (CD-ROMs), compact disk writable memories (CD-R, CD-RW), digital versatile discs or digital video discs (DVDs) (e.g., DVD-ROMs and DVD+RW), Zip disks, or USB memory devices, e.g., thumb drives or flash cards, may be coupled to bus 101 via corresponding drives, ports, or slots.

Embodiments of the present invention may be implemented using a combination of one or more modules. For example, embodiments provide for a graphical user interface module to convey results and take instructions, a general-purpose or special-purpose "communications module" for interfacing with a user application with a remote analysis platform, an "EEG data module" to collect EEG data, an "EMR access module" to access electronic medical records, various report modules to generate summaries of the statistical analysis results, as well as other modules for providing various functionality needed by embodiments of the present invention. Still yet, embodiments may incorporate two or more of these, or other, modules into a single module and/or associate a portion of the functionality of one or more of these modules with a different module.

Illustrative embodiments of statistical analysis tools are described and set forth below. This illustration is not intended to be exhaustive, but rather to highlight some of the benefits and advantages associated with various embodiments and features of the statistical analysis tools.

Once patient medical data (e.g., electroencephalogram (EEG) data) is received, it can be statistically characterized by calculating normative variations of the patient medical data with medical data of a base group. Access to one or more articles in the digital library can be provided based on the statistical characterization of the patient medical data. In some cases, the articles suggest one or more possible interpretations of the statistical characterization of the patient medical data.

The digital library has access to multiple publications or other types of information vehicles relating to interpreting medical data and possible diseases associated with medical data. Examples of the types of publications and information vehicles stored in, or accessible through, the digital library include, but are not limited to, books, scientific research articles, scientific research manuscripts, videos, audio files, tables and/or summaries of one or more information vehicles, desk references, and the like. The digital library, in some embodiments, is communicably coupled to the medical device through a user application interface that has one or more data relations for which a statistical characterization can be generated.

The statistical characterization module is designed to statistically characterize the medical data collected by the medical device against a base set of normal data. The normal data from which a base group can be selected may be stored in a normal database, for example. Once the medical data is collected by the medical device, the statistical characterization module computes if one or more out-of-variance data relations exists.

The digital library interface module automatically receives the collected medical data and any out-of-variance data relations. Once the out-of-variance data relations are received, the digital library interface module causes a search of the digital library for publications or other information vehicles relating to the collected medical data and interpretations of the one or more out-of-variance data relations. The results of the search are sent to a display module that causes the related publications or information vehicles returned from the search to be displayed to the user (e.g., on a display device, in a report, etc.)

In some embodiments, the system can include a patient medical records module communicably coupled to the digital library interface. The patient medical records module accesses additional medical and demographic data about the patient. The digital library interface module searches the digital library based in part on the additional medical and demographic data.

A base group module may be included in various embodiments of the present invention. The base group module is operable to receive demographic information about the patient and determine a base set of normal data by accessing a normative database and retrieving medical data from normal subjects with demographic information similar to the patient.

Some embodiments provide for a method for assessing brain wellness that includes receiving test subject electroencephalogram (EEG) data from a test subject. Test subject demographic information is used to index into a correlation database to access normal subject EEG data and mental assessments, wherein the correlation database contains EEG data, physiological traits, and mental traits taken from a plurality of normal human subjects associated with various ranges of demographic information.

The EEG data received from the test subject then is statistically characterized against the normal subject EEG data. One or more aspects of the statistically characterized test subject EEG data that are out-of-variance are identified. The one or more aspects then are used to access articles in a digital library relating to potential mental or physical ailments associated with the statistically characterized test subject EEG data.

In one or more embodiments, a predictive ailment report may be generated that contains a list of potential mental and/or physical ailments. A treatment report may also be generated in some embodiments that contains one or more treatment plans for the list of potential mental or physical ailments in the predictive ailment report.

Various embodiments of the present invention include a receiving operation, where a diagnosis and/or treatment plan is received from a doctor or user. The diagnosis can be stored and correlated with statistically characterized test subject EEG data. In some embodiments, the treatment is associated with the statistically characterized test subject data. After a test subject has begun, substantially completed, or completed the treatment, a second set of test subject EEG data can be collected from the test subject. The second test subject EEG data can be statistically characterized based on the normal subject EEG data and a determination can be made as to the effectiveness of the treatment using, at least in part, the statistical characterization.

Figure 1B:
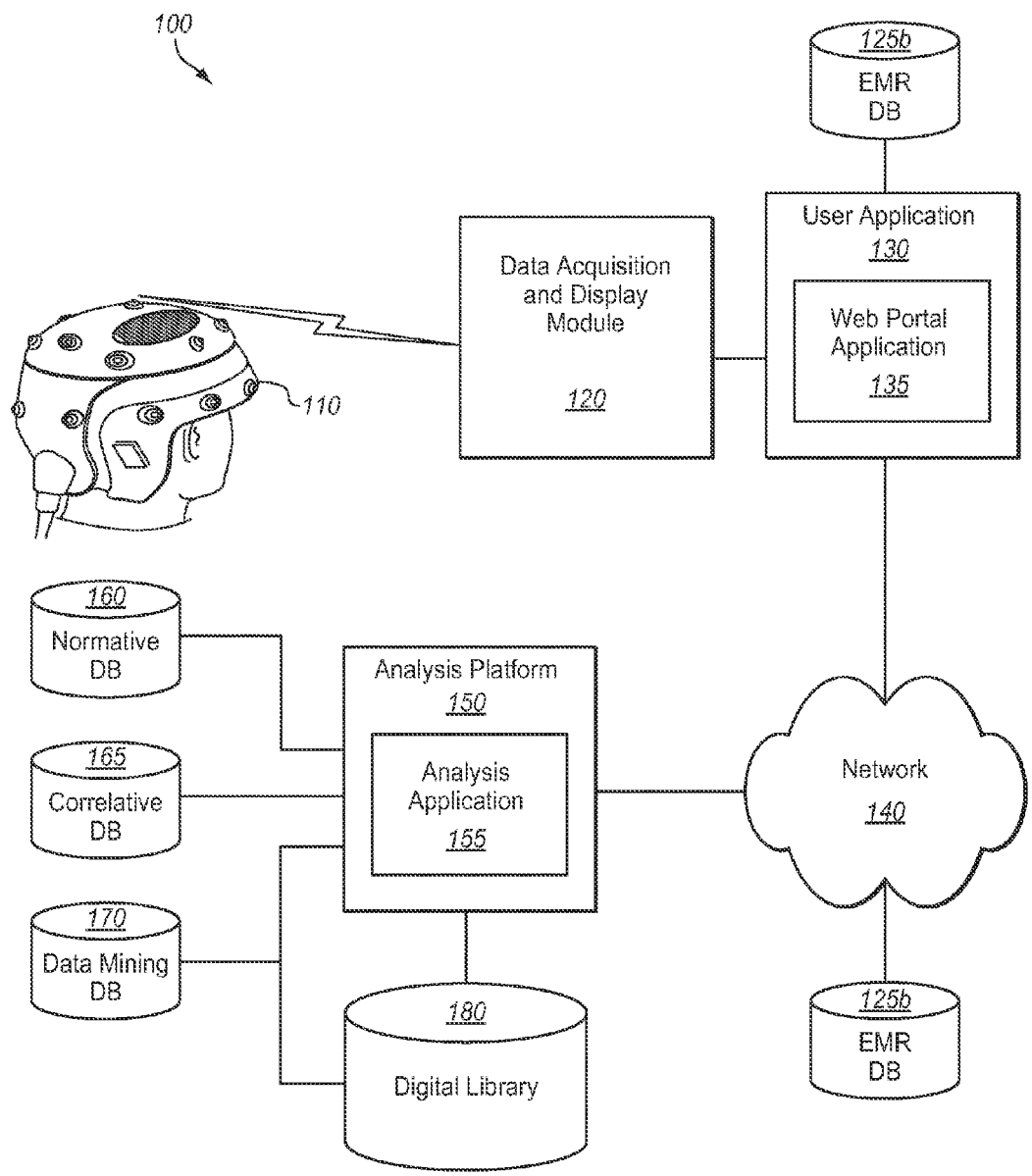
FIG. 1B is a high-level block diagram illustrating various component of an EEG data collection system in accordance with one or more embodiments of the present invention.

FIG. 1B illustrates an example operating environment 100 in which embodiments of the present invention may be utilized. The embodiments of the operating environment illustrated in FIG. 1B include a wireless helmet-like transducer 110, a data acquisition and display module 120, one or more electronic medical records 125, a user application 130, web portal application 135, a network 140, an analysis platform 150, an analysis application 155, a normative database 160, a correlative database 165, a data mining database 170, and a digital library 180. Some embodiments may combine one or more of these components into a single component. Similarly, some embodiments may combine the functionality associated with one or more of these components with another component.

In the embodiments shown in FIG. 1B, analysis platform 150 is a remote analysis platform that is accessed through a network 140. However, in some embodiments, analysis platform 150 and the various databases are co-located, and could even be integrated, with the user application 130. While not shown in FIG. 1B, embodiments of the present invention provide that remote analysis platform 150 may be communicably coupled to multiple user applications 130. Similarly, in some embodiments, user application 130 may be coupled to multiple data acquisition and display modules 120 and wireless helmet-like transducer 110.

When analysis platform 150 is servicing multiple user applications 130, the requests could be processed in a first in, first out (FIFO) manner. In other embodiments, each user application may be associated with a tier of service that could be purchased. As such, the higher tiers would have a higher priority over the lower tiers of service. In addition, some embodiments provide that the user application 130 can be associated with a set of processing rules. For example, only process requests at night, after a certain number of requests have been received, process as soon as possible, process with lowest cost, etc. For example, if there are peak times (e.g., 10:00 am to 4:00 pm) of requests associated with analysis platform 150, a higher charge could be applied for services delivered during this period. Similarly, a lower cost could be associated with off-peak times.

User application 130 can also be a smart-client type application according to one or more embodiments of the present invention. A user application 130 which is a smart-client application could utilize a local version of analysis platform 150, digital library 180, and/or the various databases to perform the analysis of the EEG data locally. In these embodiments, for example, the local versions of the software, databases, and digital library could be updated nightly, periodically, or on command. The local versions of these components may include all of the functionality and/or information available in the remote systems, digital library, and/or databases. In some cases, the local versions of these components may only include a part of the functionality of the remote systems, digital library, and/or databases. As such, if information is needed that is not available locally, the analysis could be transferred to the remote analysis platform 150 or additional data, information, etc. could be requested from the databases and/or digital library. For example, a local version of the normal database may only include Gaussian distributions of commonly used data relations and none of the raw data. Consequently, if a data relation is requested for analysis that is different than one of the ones stored locally, the normal Gaussian distribution would be accessed, or computed, at the remote site for that data relation and transferred back to the smart-client.

Wireless helmet-like transducer 110 is designed for acquiring EEG data from a patient. Embodiments of the present invention provide that the helmet-like transducer 110 record nineteen channels of EEG activity and wirelessly transfer the data to data acquisition and display module 120. The nineteen electrodes can be selected from or arranged in the International 10-20 System (see FIG. 16), for example. Some embodiments provide for more or less channels and different arrangements of the electrodes. In other embodiments, the helmet may use a wire-type transfer system to transfer the data to module 120. In some embodiments, wireless helmet-like transducer 110 includes a memory store for temporary storage of EEG data. Then, using a radio transmitter, a flash drive, or even a cable, for example, the data can be transferred to another device for analysis and/or more permanent storage. In some cases, the memory store may be a removable drive (e.g., a USB flash drive) that can be read by a computer in order to facilitate the transfer of data.

Typically, one electrode contacts the scalp for each channel and will be capable of detecting voltage potential in response to brain activity. In some embodiments, the electrodes will be able to detect a voltage potential between ten and one hundred micro-volts in response to brain activity. Each electrode may be connected to one or more gain modules for amplifying the raw signal into a range more suitable for analysis by other components. For example, each electrode could be connected to an analog gain circuit for amplification.

According to some embodiments, after amplification, the EEG signal could be processed by an analog low-pass filter that eliminates all frequencies above a certain range (e.g., 128 Hz) while leaving other frequencies virtually unchanged (e.g., below 32 Hz). The output from the analog low-pass filter then can be quantized and sampled. For example, the output of the filter can be converted from the amplified voltage, an analog value, into a 12-bit number at a rate of 256 samples per second.

Each of the EEG channels could be processed simultaneously or sequentially in accordance with various embodiments of the present invention. After processing, the digital data can be collated in a predetermined order and the data down-sampled to 128 Hz. In some embodiments, the data then will be stamped with a cyclic redundancy check code to detect any transmission errors and encrypted to prevent interception of the data. The encrypted data then can be transmitted to data acquisition and display module 120 that will acquire, decode, and display a portion of the EEG data (e.g., 30-second sample).

Data acquisition and display module 120, according to embodiments of the present invention, is configured to control the wireless helmet-like transducer in acquiring the EEG data from the patient. Module 120 may also be configured, according to various embodiments, to perform a real-time quality check analysis of the EEG data. In order to ensure that the necessary amount of good EEG data is collected, the technician or clinician can be alerted as to the quality of the collected EEG data from the data acquisition and display module. The alert could be in any form that conveys information to the user. For example, the alert could be an audible alert, a visual symbol, a print out summarizing the quality, and the like. In some cases, the quality check analysis is used to automatically end the data collection if all of the quality protocols are met.

In one or more embodiments, when the raw EEG data is received from helmet 110, the EEG data then is processed by artifact-removal software to remove artifacts (e.g., electrical signals from muscle movement) to ensure that proper data was collected. Module 120 can also cause the data to be recorded on one or more memory stores for later retrieval, load EEG data stored in one or more memory stores, and/or cause the EEG data to be displayed in one or more user-selected formats (e.g., in a raw waveform, a topographic map, a compressed spectral array, etc.).

Once the EEG data is processed by module 120, the data then is transferred to user application 130. User application 130, according to various embodiments, may include web-portal application 135 to connect to remote analysis platform 150 through network 140. Network 140 can be any group of interconnected devices capable of exchanging information from one entity to another. For example, network 140 may be a Local Area Network (LAN) or as large as the Internet. In some cases, a network 140 may be comprised of multiple networks, even multiple heterogeneous networks, such as one or more border networks, voice networks, broadband networks, service provider networks, and/or Internet Service Provider (ISP) networks interconnected via gateways operable to facilitate communications between and among the various networks. Still yet, in some cases, network 140 may be as simple as a single connection between user application 130 and analysis platform 150.

In some embodiments, user application 130 can be associated with a terminal or display that allows one or more user interface screens to be displayed. Examples of user interface screens that can be displayed through user application 130 include, but are not limited to, a patient medical data user interface screen, a data relation setup user interface screen, a data selection user interface screen, digital library interface screen, report user interface screen, and a diagnosis user interface screen.

In accordance with various embodiments, a patient medical data user interface screen can be displayed that is configured to receive medical data about a patient from either a manual input or automatically from an electronic medical record (EMR). The electronic medical records can be stored in a local memory store or in an EMR database, such as EMR databases 125a and 125b.

A data relation setup user interface screen can also be displayed in accordance with one or more embodiments of the present invention. In some embodiments, the data relation setup user interface screen allows the user to select, input, and/or search for one or more data relations to be used in the statistical characterization of the EEG data acquired from helmet 110. According to embodiments of the present invention, the one or more data relations can include functions of EEG data channels and/or extracted EEG features. For example, a user interested in identifying attention deficit disorder (ADD) could set up a data relation with the ratio of theta/beta at site Cz. As another example, a user interested in identifying depression could set up a data relation of the difference between FP1 and FP2 voltages. Examples of extracted EEG features include, but are not limited to, the spectral power for each of the EEG frequency bands (i.e., alpha, beta, gamma, theta, and delta) and evoked response potentials. These data relations set up by the user are computed and statistically compared to reference group data stored in a normative database.

In response to receiving one or more sets of EEG data relating to a test subject, a data selection user interface screen can be displayed that allows for the one or more sets of EEG data to be displayed in a raw data format, a topographic format, a trend analysis format, a spectral power format, a statistical characterization format, and/or the like. The data selection user interface screen in various embodiments allows the user to select a desired display format and change between display formats through the use of one or more radio buttons, drop-down menus, or other selection vehicles. In some cases, the data selection user interface screen allows the user to select a portion of the data collected which will be analyzed and/or displayed. For example, if a large amount of EEG data is collected under a variety of test conditions, the user could select the portion of the EEG data for analysis that is desired by the user.

The digital library user interface screen can be generated, in accordance with one or more embodiments of the present invention, that presents articles, links to articles, summaries of articles, or other information vehicles retrieved from a digital library 180. In some cases, the articles, links to articles, or summaries of articles relate to interpreting the one or more sets of EEG data. The digital library user interface screen allows the user to search digital library 180 for one or more data relations relating to particular ailments and/or conditions of interest to the user. For example, the user could search for data relations which might indicate Alzheimer's, ADD, depression, or the like when statistically compared to the normal EEG data stored in normative database 160.

Once an analysis of the data relations has been performed, the report user interface screen can be displayed on the terminal. The report user interface screen could include a predictive ailment report containing a list of potential mental or physical ailments and/or a treatment report containing one or more treatment plans for the list of potential mental or physical ailments in the predictive ailment report. In some embodiments, the diagnostic user interface screen can be displayed on the terminal with one or more input and/or selection areas that allows for a doctor to input a diagnosis, the doctor's reasoning, and/or one or more prescribed treatment plans.

Once the patient EEG data is collected and the desired data relations are evaluated, along with other pre-set data relations, the EEG data, demographic information, data relation evaluations, and the like are transferred to analysis platform 150. In some embodiments, analysis platform 150 is a web-based Internet appliance that is further configured to evaluate a set of critical variables, compare the critical variables to a set of normal EEG data stored in a normative database, calculate one or more ailment indicators, and display the results to aid a physician in mental assessment.

According to various embodiments, the desired data relations, along with other pre-set data relations, the EEG data, demographic information, data relation evaluations, and the like are used to generate a statistical analysis of the EEG data. For example, in some embodiments, the data relation evaluations are compared with age-matched reference group data stored in normative database 160 by using Gaussian distance statistics. The system, in some embodiments, can also compare the patient EEG data with an age-matched reference correlative database 165 composed of EEG data correlated to psychometric tests that evaluate memory, concentration, and mental flexibility.

Patient EEG data can be analyzed by statistical comparisons to data stored in normative database 160. According to various embodiments, normative database 160 is a statistically controlled, age-regressed database in which the data from matching single or multiple EEG channels has been transformed into a Gaussian distribution. EEG data is collected from normal individuals and then is stored in the normative database in either a raw format and/or as one or more Gaussian distribution of various data relations of channels or features of the EEG data collected.

Patient EEG data can also be analyzed by generating a statistical comparison to data stored in correlative database 165. According to various embodiments, correlative database 165 is a database in which various EEG features have been correlated with memory functions (e.g., short term memory, concentration, and mental flexibility) or any other psychometrics. In some embodiments, correlative database 165 is a proprietary collection of EEG data and correlated parameters which has been purchased or developed. The exact correlations and methodologies behind the correlations may or may not be disclosed to users of the database In correlative database 165, EEG data and psychometric tests results are collected from normal individuals. A correlation is made between EEG features collected from the normal individuals and the psychometric results. The EEG data, selected neuro-psychometric test results, and the correlations then are stored in correlative database 165. The data relations determined to be correlated with memory functions are evaluated for each individual, and one or more Gaussian distributions are created and stored.

In some embodiments, when the patient EEG data is analyzed using correlative database 165, the result may be presented in a performance panel on user application 130. The performance panel is intended to display the results of the correlative analysis of the patient's EEG data to standard psychometric tests that evaluate memory, concentration, and mental flexibility.

According to various embodiments, data mining database 170 includes a collection of patient data and a collection of aggregate patient data. This data can be used, for example, in the future along with additional EEG tests to determine if particular treatment plans were effective in correcting a diagnosed ailment and/or improving an individual's quality of life.

Figure 2:
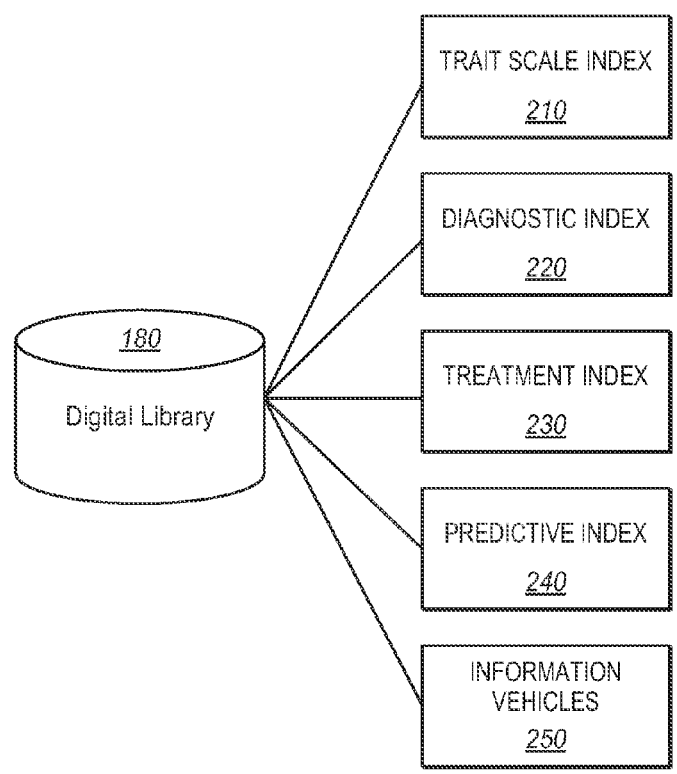
FIG. 2 is a block diagram illustrating the layout of various components of an EEG helmet in accordance with various embodiments of the present invention.

FIG. 2 is a block diagram 200 which illustrates various components which may be stored in a digital library 180 in accordance with one or more embodiments of the present invention. Embodiments of digital library 180 store various indexes and informational vehicles. Examples of the types of indexes that can be stored in digital library 180 include, but are not limited to, trait scale index 210, diagnostic index 220, treatment index 230, and predictive index 240.

According to some embodiments, trait scale index 210 is a collection of data relations (and possibly distributions of those data relations as found in members of the normal database) that have been identified from literature.

Diagnostic index 220, in accordance with various embodiments, is a set of data relations that have been correlated with diagnoses from a doctor. In some embodiments, these correlations have been developed based on data accessed through the aggregated patient database and stored in data mining database 170. Diagnostic index 220 may also include distributions of the data relations and may also be computed information of normal EEG data found in normal database 160. In some embodiments of the present invention, out-of-variance data relations found during the statistical analysis can be searched for in diagnostic index 220 in order to aid a doctor in determining the ailment of a patient.

Treatment index 230, in embodiments of the present invention, is a collection of treatments which have proven effective for patients with similar EEG statistical characterizations.

Predictive index 240, in many embodiments, includes a set of data relations that have been correlated between earlier EEG data and a current diagnosis from a doctor. For example, a patient may go to a doctor and have routine EEG tests performed throughout his lifetime. In his seventies, he takes an EEG test and is diagnosed with Alzheimer's. Predictive index 240 is created by generating correlations between this and other patients' earlier test data and the current diagnosis of Alzheimer's to find early indicators.

In accordance with one or more embodiments, digital library 180 has access to multiple publications or other types of information vehicles 250 relating to interpreting medical data and possible diseases associated with medical data. Examples of the types of publications and information vehicles stored in or accessible to the digital library include, but are not limited to, books, scientific research articles, scientific research manuscripts, videos, audio files, tables, and/or summaries of one or more information vehicles, desk references, and the like. Digital library 180, in some embodiments, is communicably coupled to the medical device through a user application interface that has one or more data relations for which a statistical characterization of the acquired medical data can be generated.

In some embodiments, digital library 180 can store one or more user application interfaces which can be loaded directly into user application 130. For example, a specialist in the field of depression could create a user application interface that has data relations the specialist would be interested in using during the statistical characterization of the EEG data.

Figure 3:
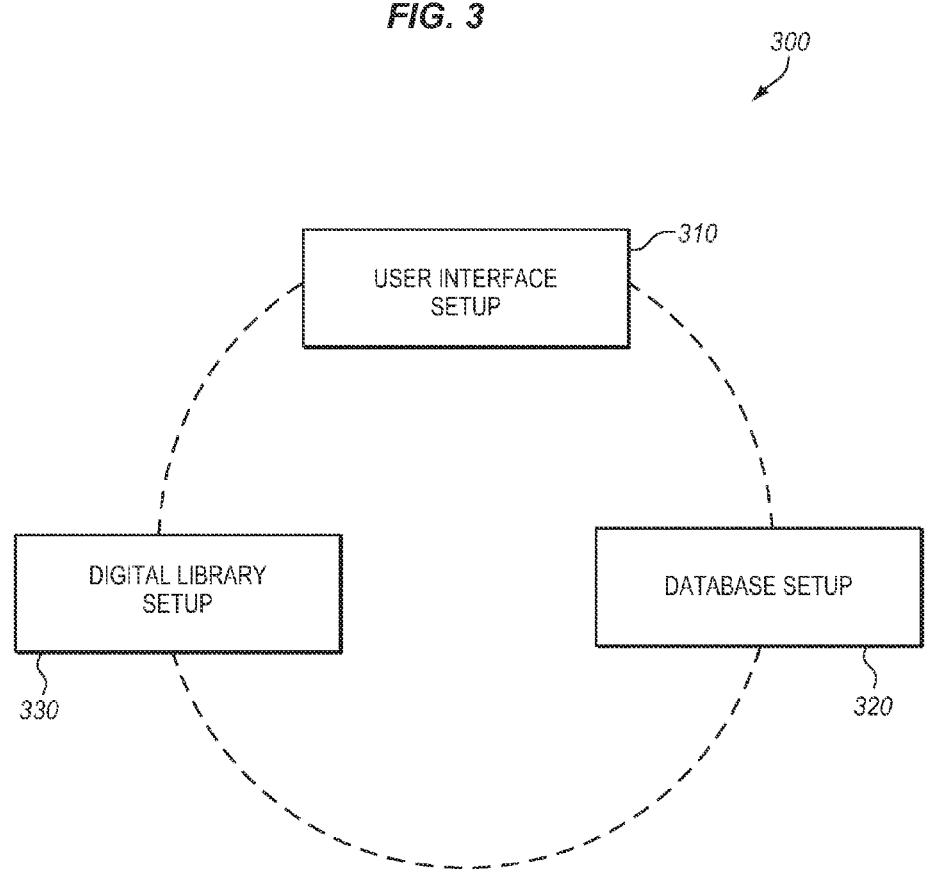
FIG. 3 illustrates an example of a computer system with which embodiments of the present invention may be utilized.

FIG. 3 illustrates an overview of the setup 300 of the systems in accordance with various embodiments of the present invention. Embodiments of the EEG data collection and analysis system 100 can be set up by using user interface setup operation 310, database setup operation 320, and digital library setup operation 330. Various embodiments of these setup operations are described in more detail in FIGS. 4-14.

FIG. 4 is a flow chart illustrating operations 310 for setting up or updating a user application interface which may be used in accordance with some embodiments of the present invention. In the embodiments illustrated in FIG. 4, a user first determines an ailment or condition of interest at ailment operation 410. For example, when a patient arrives at a doctor's office, the doctor can make an initial assessment of the patient and determine that the patient may have a certain ailment or condition (e.g., depression). In other situations, the doctor could have decided that he wants to screen all his patients for a certain ailment (e.g., attention deficit disorder). Still yet, selections of certain ailments could occur automatically. For example, the doctor could select that all previous diagnoses in the patient's electronic medical records be retested and/or monitored.

Upon deciding ailment(s) of interest, the doctor can set up the user application 130, or load a pre-existing interface setup, to determine if the EEG data is indicative of the ailment of interest. To this end, the doctor also can access the digital library and search, using searching operation 420, for the ailment of interest (e.g., depression). The search typically returns articles which provide one or more data relations, in suggestion operation 430, that when statistically compared to a base group of normal subjects has been shown to indicate the ailment. The doctor can review the articles or other informational vehicles and decide in decision operation 440 whether to accept or reject the data relations in a particular article. If the doctor rejects the data relation, then the user application interface is not updated using no-update operation 450. In addition to searching for articles which indicate data relations for a particular ailment, the doctor can use his personal knowledge about EEG data to set up data relations to be compared to the normal group using personal update 470. Still yet, some embodiments provide that the doctor can search for and load pre-designed expert interfaces with data relations that have been developed by experts in the field using expert interface operation 480. Whether the user selects data relations from the digital library, enters data relations based on personal knowledge, and/or accepts a pre-designed expert interface, the application interface is appropriately updated.

Figure 5A:
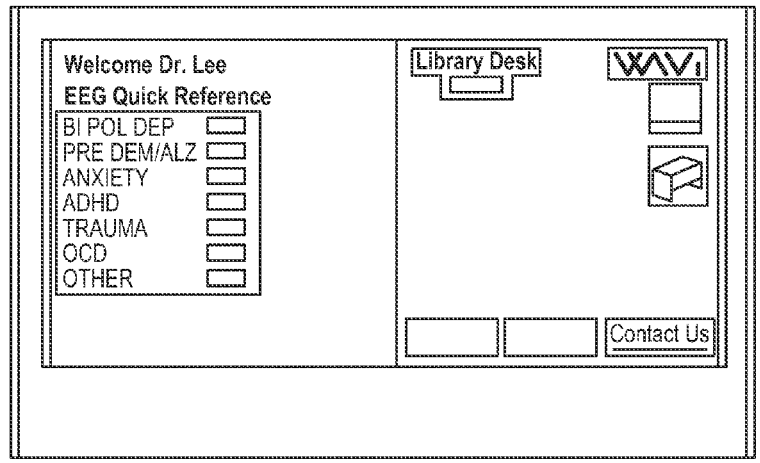
FIGS. 5A and 5B are examples of snapshots of displays that may be used in accordance with one or more embodiments of the user application interface.
Figure 5B:
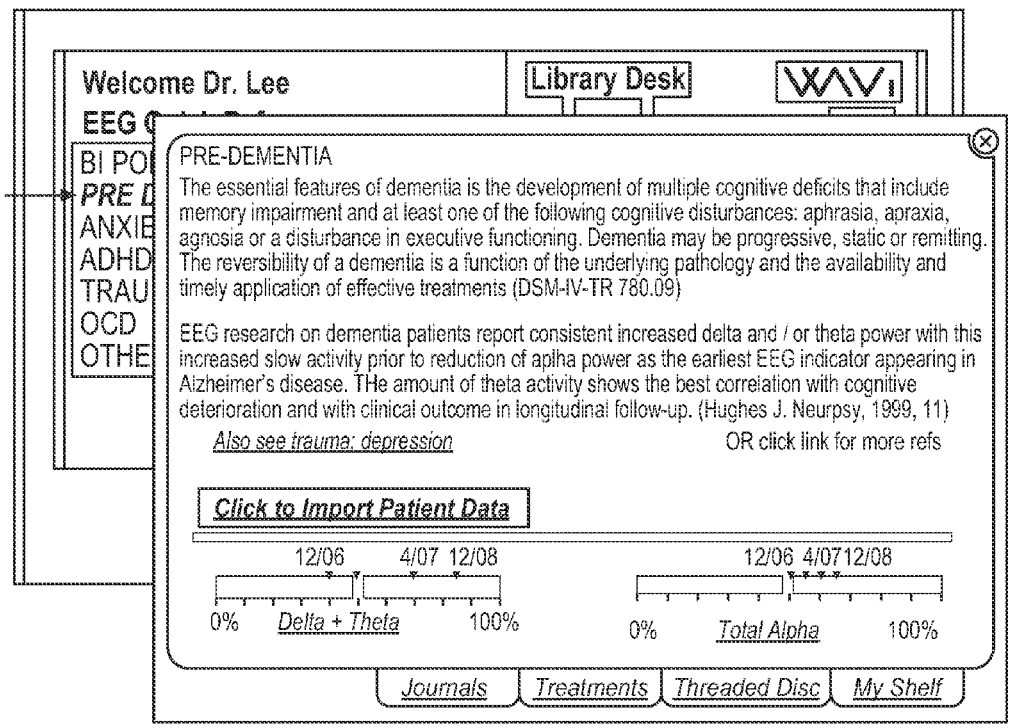

FIGS. 5A and 5B are examples of snapshots of displays that may be used in accordance with one or more embodiments of the user application interface.

Figure 6:
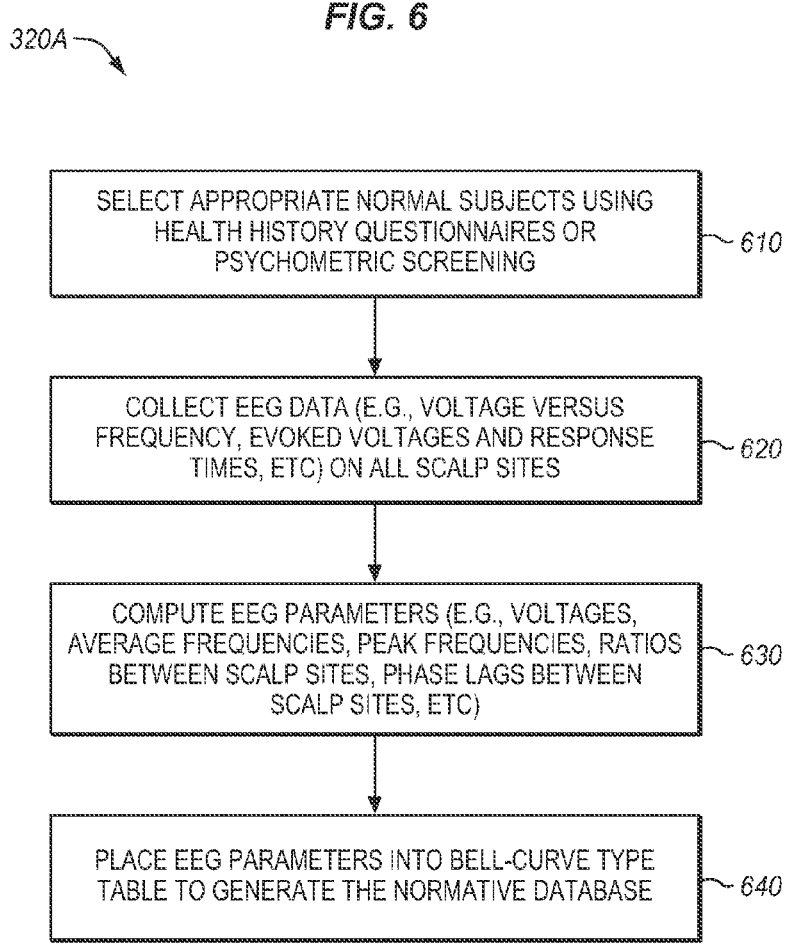
FIG. 6 is a flow chart illustrating a set of operations 320A for generating a normative database 160 in accordance with various embodiments of the present invention.

FIG. 6 is a flow chart illustrating a set of operations 320A for generating a normative database 160 in accordance with various embodiments of the present invention. In various embodiments, normative database 160 stores EEG data and/or Gaussian distributions of EEG data features or parameters from a set of normal individuals. Selection operation 610 determines a set of normal individuals using health history questionnaires and/or psychometric screening. For example, a health history questionnaire may screen for people who have no head injuries, are not on any medications, have an absence of known diseases, and the like. A psychometric screening process can be used in some embodiments to screen out individuals with one or more mental conditions (e.g., Axis I and Axis II disorders).

In some cases, selection operation 610 could be performed using a clinical study. The clinical study could be designed to obtain mental function data from a set number (e.g., 520) of normal, non-clinically impaired subjects by using EEG and neuropsychological testing. To ensure reliable data for normative database 160, the study design could include at least one interim assessment of the EEG data. In addition, the study population could be increased until consistent split-half replication is achieved. For example, Spearman-Brown's coefficient could be used to evaluate the association between split-half replications for each measure. Other possible study considerations include, but are not limited to, the inclusion/exclusion criteria to identify a normal population, sufficient age coverage across the average life-span (e.g., 18-90 years), sufficient artifact-free EEG data for analysis, and methodologies for standardization. Once the clinical study is completed, parallel partial correlation analysis could be used to eliminate any systematic effects of age, sex, and handedness.

In other embodiments, smaller clinical studies (e.g., N<20) could be used in conjunction with resampling methods, such as bootstrapping, to generate distributions of various EEG features and/or data relations. For example, a computer model of an approximating distribution, such as an empirical distribution of observed data, could be set up. The computer model could use bootstrapping methods to sample from the approximating distribution and allow for the estimation of various statistical properties. One advantage of using bootstrapping methods is that the normality assumption is not required.

According to various embodiments, EEG data from normal individuals then is collected using collection operation 620. The EEG data can be collected under eyes-closed resting conditions, eyes closed—auditory active conditions, and the like. While the amount of EEG data collected can vary, in some cases, the amount of EEG data collected for each individual is between thirty seconds and ten minutes. Once a set of normal EEG data is collected on all scalp sites from a variety of normal individuals, various EEG parameters are computed using computation operation 630. Examples of EEG parameters which can be computed during computation operation 630 include, but are not limited to, voltages, average frequencies, peak frequencies, ratios between scalp sites, phase lags between scalp sites, and the like.

Once the various EEG parameters are computed, placing operation 640 generates a Gaussian distribution of these features which then are stored in normative database 160. In some embodiments, multiple Gaussian distribution of these features can be created using normal individuals with one or more similar characteristics, such as age ranges (e.g., 18 to 20, 21 to 30, 31 to 40, 41 to 50, etc.), right handedness, left handedness, native language, race, culture, gender, weight, height, smoking habits, alcohol consumption habits, use of non-medication supplements, use of hormone therapies, pregnancy testing (for female subjects), education level, hearing ability, vision, and the like. Each distribution can be tagged with metadata indicating the similar characteristics which were used to create the distribution. The metadata can be used later in searching normative database 160 to find a Gaussian distribution created with characteristics similar to a current test subject.

Normative database 160, according to many embodiments, could also be validated using one or more validation tests. The one or more validation tests can be designed to test one or more of the following: normality, culture-fairness, reliability, comparability to published replication, and an adequate demonstration of sensitivity and specificity.

Figure 7:
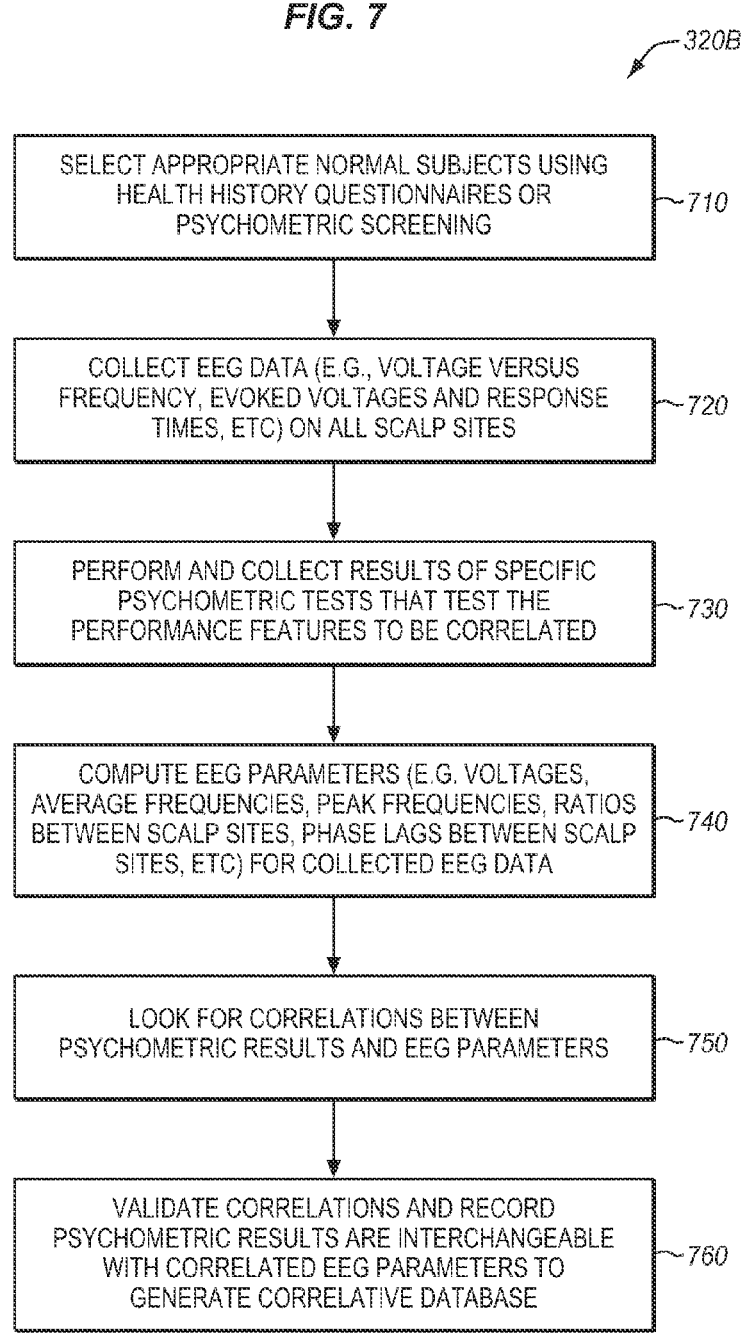
FIG. 7 is a flow chart illustrating a set of operations 320B for generating a correlative database 165 in accordance with one or more embodiments of the present invention.

FIG. 7 is a flow chart illustrating a set of operations 320B for generating a correlative database 165 in accordance with one or more embodiments of the present invention. According to various embodiments, correlative database 165 stores EEG data or Gaussian distributions of EEG data features or parameters from a set of normal individuals. Selection operation 710 determines a set of normal individuals using health history questionnaires and/or psychometric screening similar to selection operation 610. However, different standards, clinical test variations (e.g., group size, screening criteria, and the like) may be used. While not necessary, in many cases, the same individuals may be used for generating data for normative database 160 and correlative database 165.

According to various embodiments, EEG data from normal individuals is collected using collection operation 720. Collection operation 720 can include one or more EEG data collection routines. For example, in some embodiments, EEG data is collected under eyes-closed resting conditions for a period of ten minutes. Then, eyes closed—auditory active EEG data is collected in the presence of an auditory stimulus for ten minutes. The auditory stimulus can be a standard oddball task, where the subject will be randomly presented with a series of high frequency tones. Instructions can be presented and the subject instructed to press a button with the index finger of each hand in response to the high target tones and to ignore the lower tones. The amount of EEG data and conditions under which the collection of the EEG data is collected can vary in different embodiments of the present invention.

During testing operation 730, the normal subjects take a battery of neuropsychological test to measure memory, concentration, and mental flexibility. In some embodiments, the neuropsychological tests consist of the following: Digit Span and Letter-Number Sequencing Tests from the WMS-III to measure memory; the CPT-II to measure concentration; the WCST to measure mental flexibility; and the Stroop Task to confirm mental flexibility and concentration. However, other tests known to those of ordinary skill in the art may be used. In some cases, these tests are administered by a trained clinician to ensure that test subject fatigue does not affect the tests results.

Once a set of normal EEG data is collected on all scalp sites from a variety of normal individual, various EEG parameters are computed using computation operation 740. Examples of EEG parameters which can be computed during computation operation 740 include, but are not limited to, voltages, average frequencies, peak frequencies, ratios between scalp sites, phase lags between scalp sites, and the like.

The neuropsychological test results are collected and the EEG data is processed. Correlating operation 750 then determines correlations between the test results and EEG parameters. The correlations between the test results and the EEG parameters are validated (e.g., using information in data mining database 170) and recorded in correlative database 165 using validation operation 760.

Figure 8:
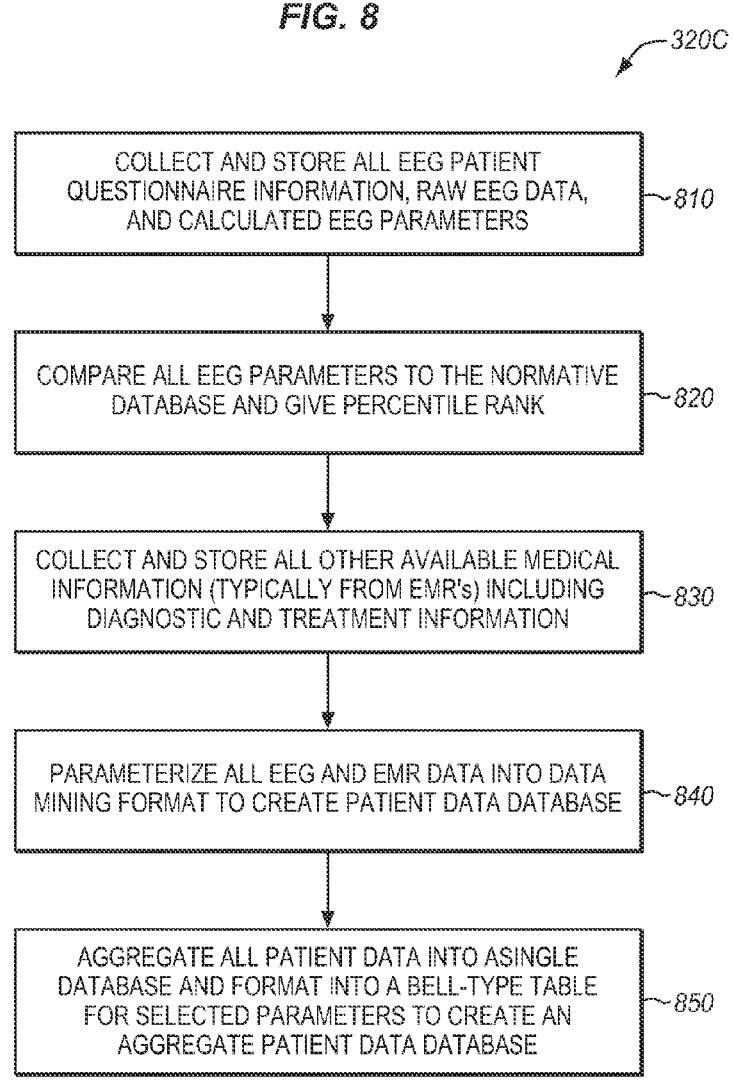
FIG. 8 is a flow chart illustrating a set of operations 320C for generating a patient database in accordance with embodiments of the present invention.

FIG. 8 is a flow chart illustrating a set of operations 320C for generating a patient database in accordance with embodiments of the present invention. In some embodiments, a patient database is a subset of data stored in data mining database 170. The patient database includes all available medical information (e.g., inputs from doctors, EMR, raw EEG data, calculated parameters, and the like).

In EEG collection operation 810, all available patient EEG data is collected and stored. Collection operation 810 could be performed on a pre-set schedule (e.g., hourly, daily, weekly, etc.), after a pre-determined event (e.g., 1000 sets of new patient data are available), or upon a user request. Once the data is collected, ranking operation 820 compares all or some of the EEG parameters and/or selected data relations to the normative database and generates a percentile rank. Medical information collection operation 830 collects all other available medical information (e.g., from a patient's EMR). Examples of the type of information collected include, but are not limited to, diagnostic and treatment information. In some embodiments, collection operation 830 and EEG collection operation are combined into a single collection operation.

Once all of the data is collected, parameterization operation 840 places the EEG data and medical information into a data mining format to create the patient data database. In some embodiments, placing the data into the data mining format includes using current procedural terminology (CPT) codes from the American Medical Association. In other embodiments, any coding system that accurately describes the medical, surgical, and diagnostic services of a doctor may be used. The use uniform codes, such as the CPT codes, allows for a common condition or treatment to be represented by the same alphanumeric string and makes future correlation and searching easier.

Once parameterization operation 840 is completed, aggregation operation 850 aggregates all the patient data together into a single database. In addition, some or all of the EEG parameters and functions of EEG parameters (i.e., data relations) computed in ranking operation 820 are used to generate one or more distributions to create the patient data database.

Figure 9:
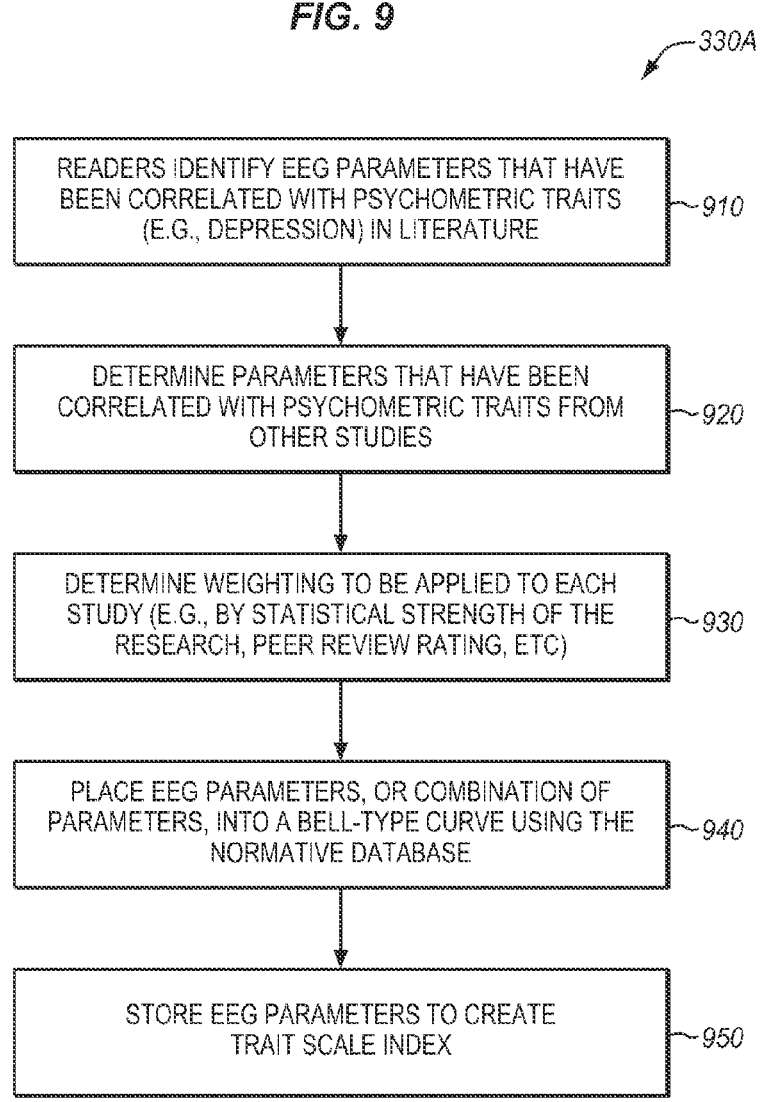
FIG. 9 is a flow chart illustrating a set of operations 330A for generating trait scale index 210 in accordance with some embodiments of the present invention.

FIG. 9 is a flow chart illustrating a set of operations 330A for generating trait scale index 210 in accordance with some embodiments of the present invention. According to various embodiments, trait scale index 210 is a collection of data relations that have been identified, extracted, and/or created from the literature that has correlated the data relations with one or more psychometric traits (e.g., depression).

Identification operation 910 identifies one or more EEG parameters and/or data relations that have been correlated with psychometric traits. According to embodiments of the present invention, identification operation 910 could be performed manually, automatically with the use of a computer (e.g., searching for key words), or through a combination of manual operations and automatic operations. Various selection criteria could be used to screen for acceptable articles. For example, in some embodiments, a ninety-five percent confidence level may be required.

A determination is made, in parameter collection operation 920, of the parameters that have been correlated with psychometric traits from other studies that have been published in the literature. In some embodiments, parameter collection operation 920 can collect parameters relating to a particular psychometric condition by creating a list of articles addressing the particular psychometric condition and correlated data relations along with other information (e.g., statistical strength of the study). A pattern extraction algorithm can be used in some embodiments to collect the parameters and look for patterns from the literature. In one embodiment, the pattern extraction algorithm calculates a trait within the literature and builds a distribution curve from the calculated normative data automatically.

In weighting operation 930, a weighting is associated with each study. In one or more embodiments of the present invention, the weighting can be determined based on the statistical strength of the research, peer review ratings, effectiveness of a certain parameter in predicting the psychometric condition, and others. Various embodiments of the present invention not only allow for data relations to be taken directly from literature but also for the creation of new data relations to come up with a better estimator or predictor of the psychometric condition. In some cases, the weight can be generated by performing a best fit on data stored in data mining database 170 which has been associated with the particular psychometric condition.

Distribution operation 940 places the EEG parameters, or combination of the EEG parameters, into a bell-type curve using normative database 160. These distributions are stored using storing operation 960 to create trait scale index 240. In some embodiments, the distributions of the EEG parameters and/or combination of the parameters are not stored (i.e., only the data relations are stored) in trait scale index 210. In those cases, the distribution can be generated when needed using normative database 160. In various embodiments, the distributions for the data relations then can be stored in normative database 160 for future access or they can be discarded and generated again as needed.

Figure 10:
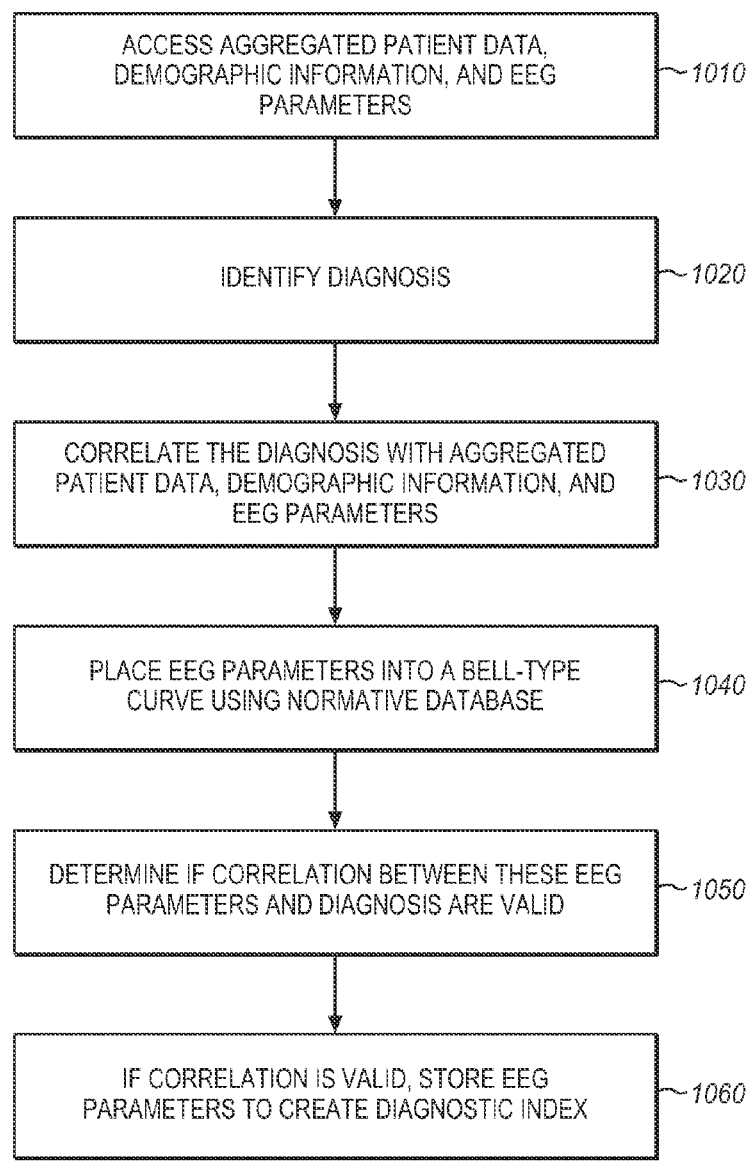
FIG. 10 is a flow chart illustrating a set of operations 330B for generating diagnostic index 220 in accordance with various embodiments of the present invention.

FIG. 10 is a flow chart illustrating a set of operations 330B for generating diagnostic index 220 in accordance with various embodiments of the present invention.

Figure 11:
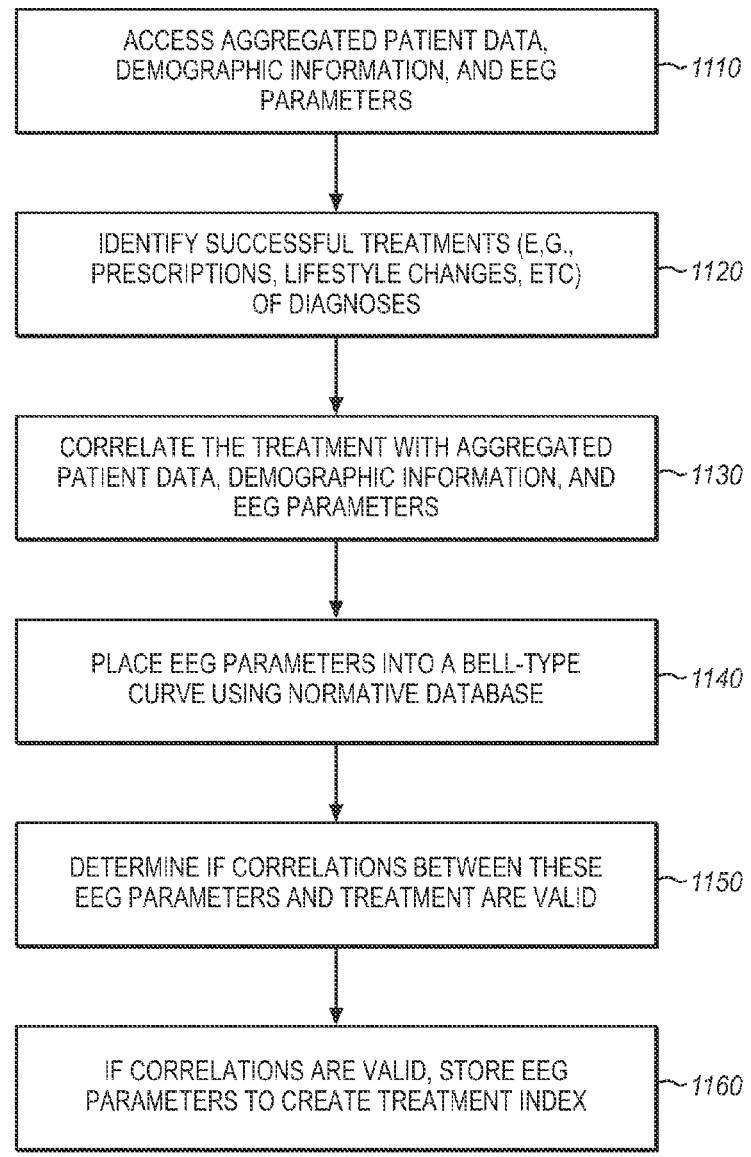
FIG. 11 is a flow chart illustrating a set of operations 330C for generating treatment index 230 in accordance with one or more embodiments of the present invention.

FIG. 11 is a flow chart illustrating a set of operations 330C for generating treatment index 230 in accordance with one or more embodiments of the present invention.

Figure 12:
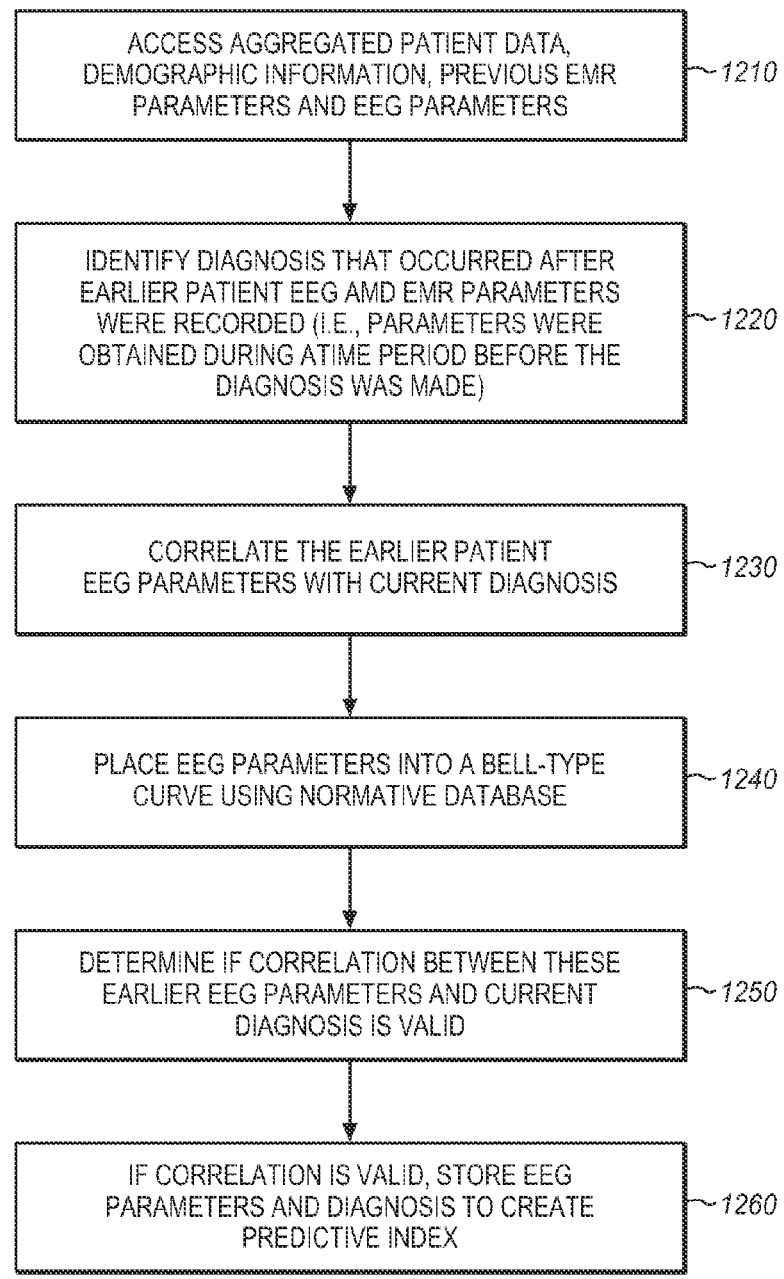
FIG. 12 is a flow chart illustrating a set of operations 330D for generating predictive index 240 in accordance with various embodiments of the present invention.

FIG. 12 is a flow chart illustrating a set of operations 330D for generating predictive index 240 in accordance with various embodiments of the present invention.

Figure 13:
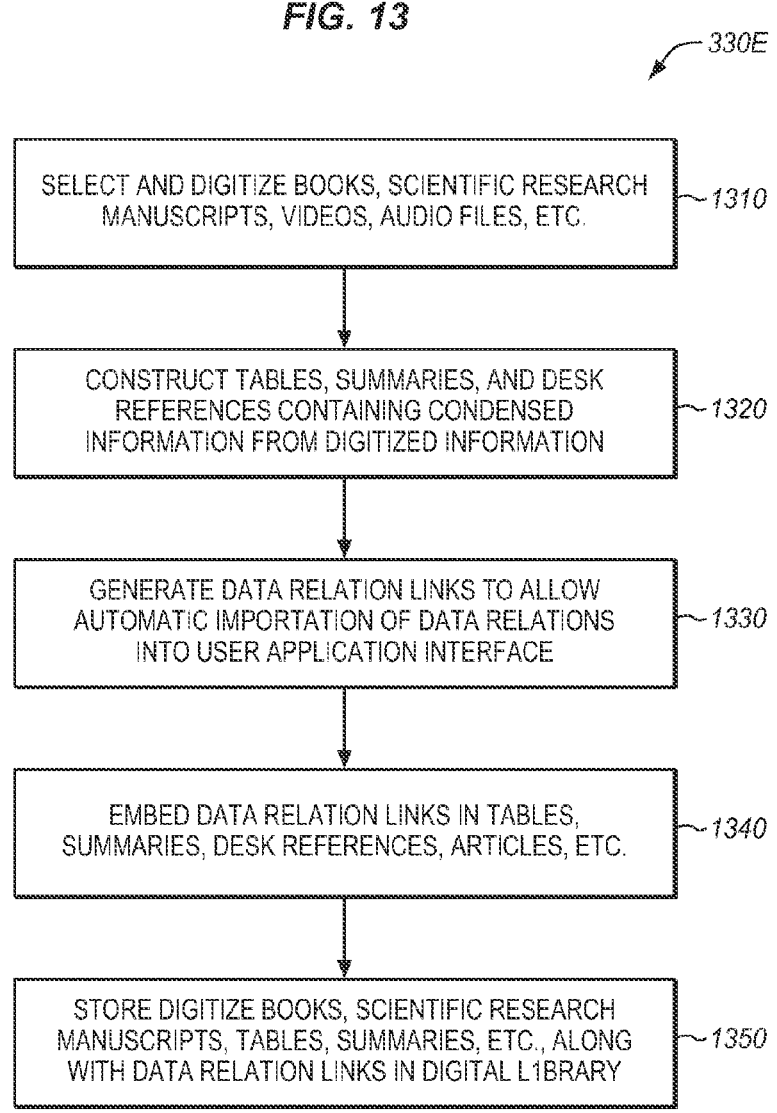
FIG. 13 is a flow chart illustrating a set of operations 330E for generating information vehicles 250 in accordance with various embodiments of the present invention.

FIG. 13 is a flow chart illustrating a set of operations 330E for generating information vehicles 250 in accordance with various embodiments of the present invention.

Figure 14:
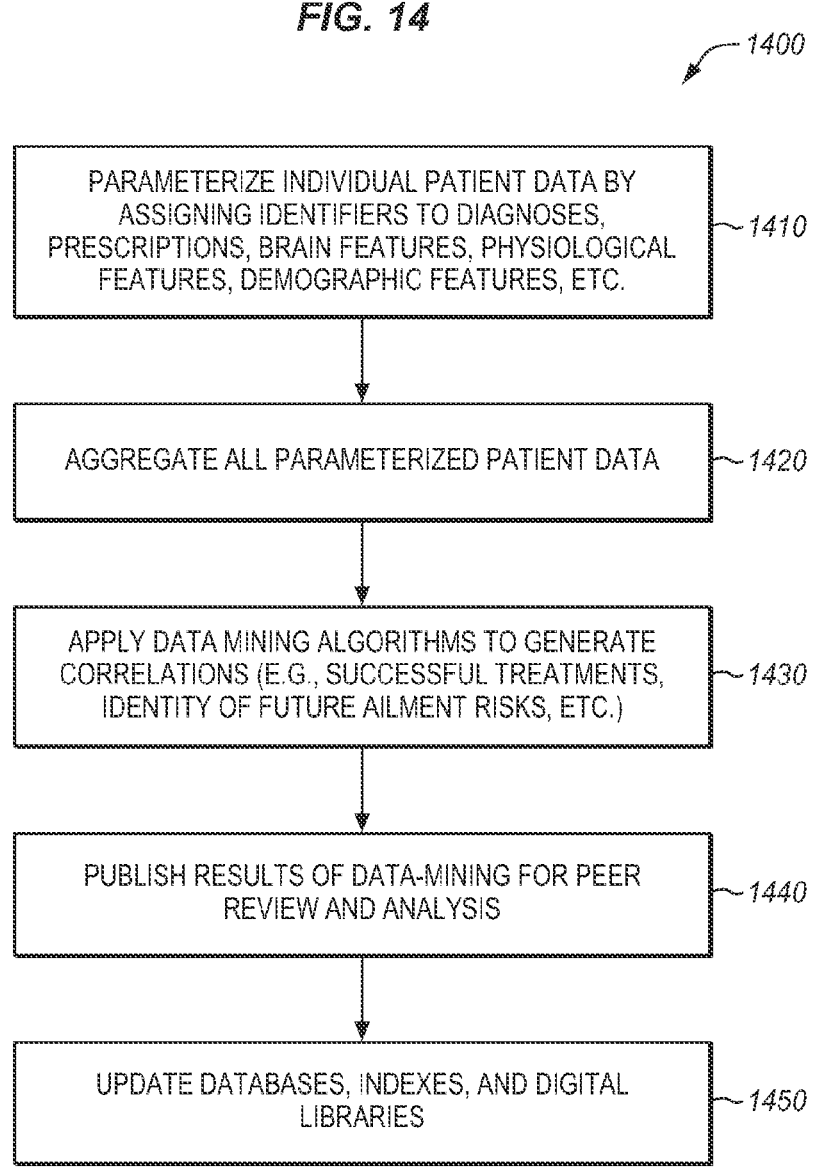
FIG. 14 is a flow chart illustrating a set of operations 1400 for updating one or more databases and/or indexes in accordance with one or more embodiments of the present invention.

FIG. 14 is a flow chart illustrating a set of operations 1400 for updating one or more databases and/or indexes in accordance with one or more embodiments of the present invention.

Figure 15:
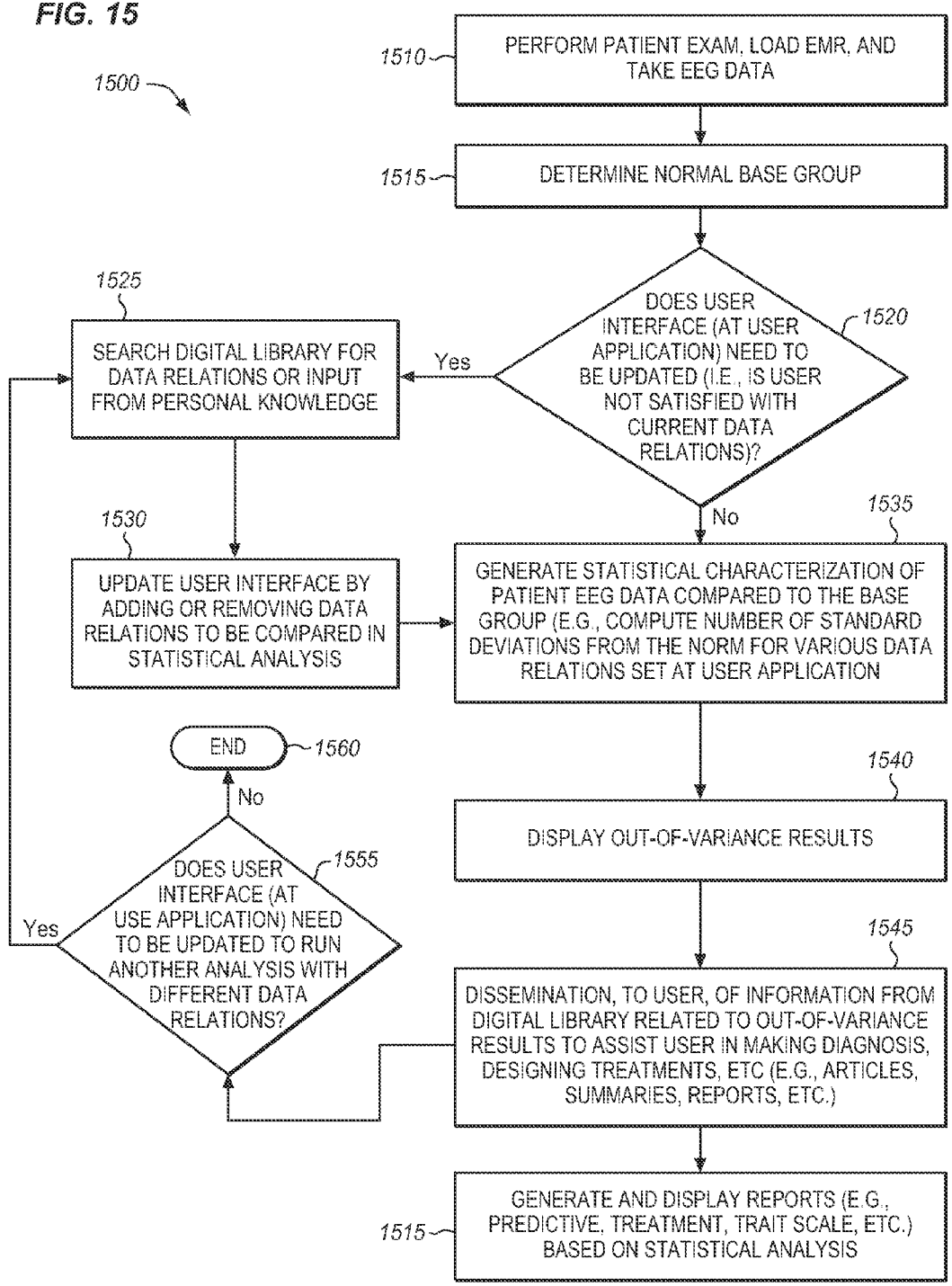
FIG. 15 is a flow chart illustrating an example of a set of operations 1500 used in accordance with various embodiments of the present invention to assist in EEG data interpretation.

FIG. 15 is a flow chart illustrating an example of a set of operations 1500 used in accordance with various embodiments of the present invention to assist in EEG data interpretation. In information collection operation 1510, when a patient arrives at a doctor's office, the doctor can perform a medical exam and make an initial assessment of the patient. Patient data is loaded into the user application interface manually or through accessing an electronic medical record (EMR) during information collection operation 1510. Examples of the types of patient information that may be entered include, but are not limited to, historical EEG data from previous collection, medical history, lifestyle information, answers to patient questionnaires, current and/or past medications, demographic information, and the like. Using the available information, the doctor determines that the patient may have a certain ailment (e.g., depression).

According to various embodiments, information collection operation 1510 also includes EEG data collection. The EEG data typically is collected by placing the electrodes on the patient's head. In some cases, a conductive liquid is applied to each electrode including any electrodes placed on the patient's earlobes for references. The use of the conductive liquid allows for an improved impedance level between the electrode and the patient's head.

The clinician then initiates an EEG test. The EEG data resulting from the test is either saved for later analysis and/or is directly transferred to the user application station. The pre-set data relations (e.g., ratio of theta/beta at site Cz) set by the doctor are evaluated using the current EEG data. The data relations, patient information, and EEG data then are transmitted to a remote analysis platform. Using base group selection operation 1515, a normal base group is selected from the normative database based on the received patient information. The patient information loaded in information collection operation 1510 can be used in selecting a base group for statistical comparison. For example, if the patient is a twenty-seven year old female, a base group may be selected from the normative database which includes normal EEG data from females with ages ranging from twenty-five to twenty-nine.

Using the available information from information collection operation 1510, the doctor determines if the user interface needs to be updated so that a statistical analysis can be performed based on data relations which have been correlated to certain ailments the doctor is interested in screening. In decision operation 1520, the doctor decides whether or not the user interface needs to be updated to include new data relations or to remove old data relations. If the user interface needs to be updated, then the process branches to input operation 1525. If the user interface does not need to be updated, the process branches to statistical characterization operation 1535.

During input operation 1525, the doctor can use his personal knowledge about EEG data to setup data relations. In some cases, the doctor can supplement his own knowledge by searching the digital library for data relations of interest. For example, the doctor can search for the ailment of interest (e.g., attention deficit disorder, attention-deficit/hyperactivity disorder (ADHD), depression, obsessive compulsive disorder, anxiety, schizophrenia, bipolar disorder, and substance abuse) to find information vehicles which include data relations that when statistically compared to a base group of normal subjects has been shown to indicate the ailment. In some embodiments, the information vehicles and indexes stored in digital library 180 provide links associated with the data relations that when selected will automatically load the data relations into user application 130. In other embodiments, the doctor can load pre-designed data relations that have been developed by experts in the field and begin modifying those if desired. Updating operation 1530 then updates the application user interface by adding or removing data relations as requested by the user. The process then branches to statistical characterization operation 1535.

Examples of data relations that may be found in various articles (or known by the doctor) include, but are not limited to, increased alpha power in the frontal cortex correlates with increased mental flexibility, whereas decreased alpha power in the frontal cortex correlates with decreased mental flexibility. The theta-to-beta power ratio has been shown to correlate with concentration and is sensitive to subtle impairments in concentration. Functionally intact memory has been shown to be predicted by high alpha power and low theta power in the occipital and temporal regions of the brain. These are just examples of the types of correlations that may be found in the information vehicles and/or indexes stored in digital library 180.

In one or more embodiments of statistical characterization operation 1535, once a base group is determined, the desired data relations then are computed for the patient EEG data, and a statistical characterization is generated by computing the number of standard deviations from the norm of the normal group. In some embodiments, differences of the patient data relations from the normal EEG activity of the base group are expressed in the form of a z-score for each frequency band. Some embodiments provide for the percentile ranking, or standard score, of the patient's EEG data as it relates to the performance of normal individuals on one or more psychometric tests. However, as will be appreciated by one of ordinary skill in the art, various other statistical methods may be used to compare the patient EEG data with that of the base group. In accordance with various embodiments, statistical characterization operation 1535 can also generate a statistical analysis of the patient EEG data against correlative databases, predictive databases, and/or one or more indexes to determine the likelihood that the patient has, or will develop, a particular ailment.

Once the statistical characterization is complete, these results can be presented to the user by display operation 1540. In embodiments of the present invention, display operation 1540 can display the results through the user application 130 by links to generated reports, quick reference color-coded scales, numerical percentiles, and/or in other display formats as will be appreciated by one of ordinary skill in the art.

In various embodiments, dissemination operation 1545 searches the digital library for information vehicles relating to the out-of-variance results determined by the statistical characterization. The results of the search can be displayed through the user application 130. In some cases, the information vehicles (e.g., articles, summaries, etc.) can be used by the doctor in making a diagnosis designing treatment options, determining possible related ailments, and/or the like.

In the embodiments illustrated in FIG. 15, after dissemination operation 1545, the process branches to report operation 1550 and/or update decision 1555. In accordance with some embodiments, report operation 1550 generates and displays reports. Examples of the types of reports which can be generated include, but are not limited to, a predictive report, a treatment report, and others. The doctor can review these reports and/or the disseminated information vehicles displayed in dissemination operation 1545 to determine if a statistical characterization of the patient's EEG data needs to be computed using different data relations. Using update decision 1555, the user decides if the user interface needs to be updated. If not, then the process branches to end operation 1560. If the user does decide the user interface needs to be updated, then the process branches back to input operation 1525.

Figure 16:
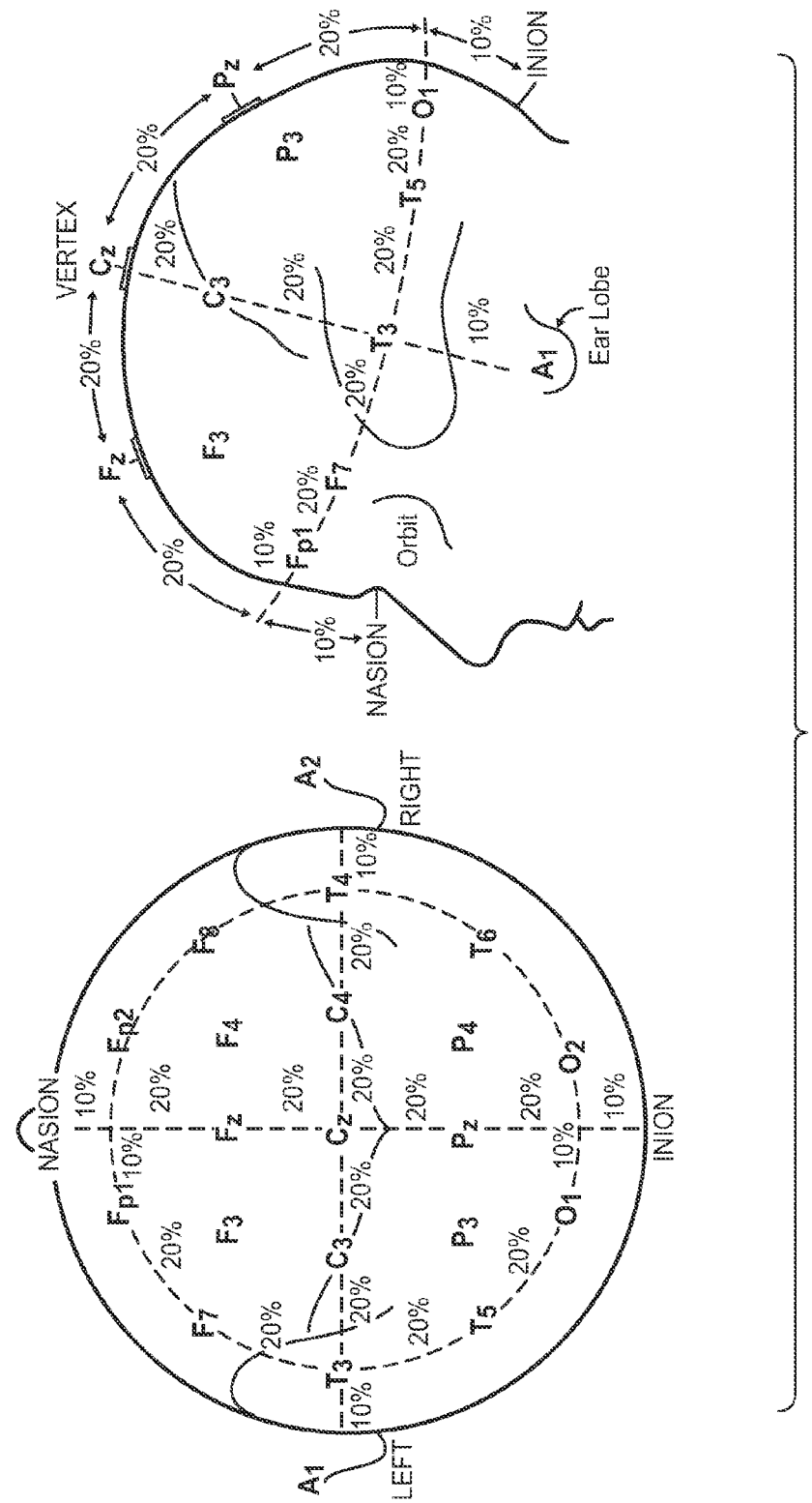
FIG. 16 is a diagram 1600 illustrating an example EEG helmet electrode placement for gathering EEG data in accordance with some embodiments of the present invention.

FIG. 16 is a diagram 1600 illustrating an example EEG helmet electrode placement for gathering EEG data in accordance with some embodiments of the present invention. FIG. 16 represents electrode placement consistent with the International 10-20 EEG Classification System. Each electrode site has a letter to identify the lobe and a number or another letter to identify the hemisphere location. The letters C, F, Fp, O, P and T stand for Central, Frontal, Frontal Pole, Occipital, Parietal, and Temporal locations of the brain, respectively. The even numbers refer to locations in the right hemisphere, the odd numbers refer locations to the left hemisphere, and the letter z refers to an electrode placed on the midline.

Figure 17A:
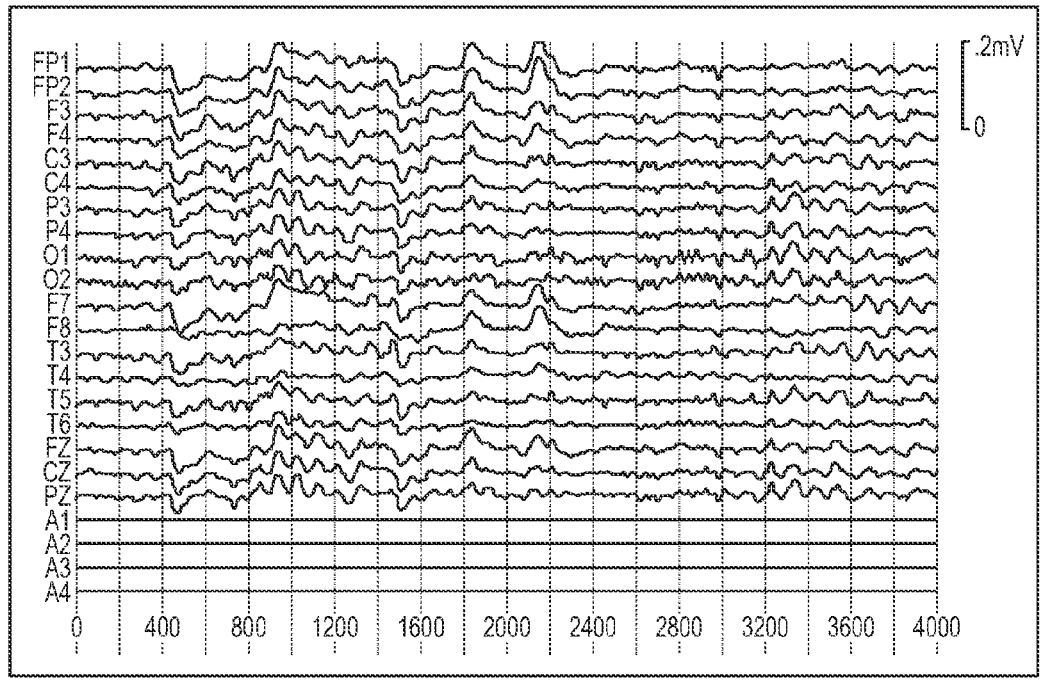
FIGS. 17A and 17B illustrate an example of EEG data that may be gathered during and EEG test in accordance with embodiments of the present invention.
Figure 17B:
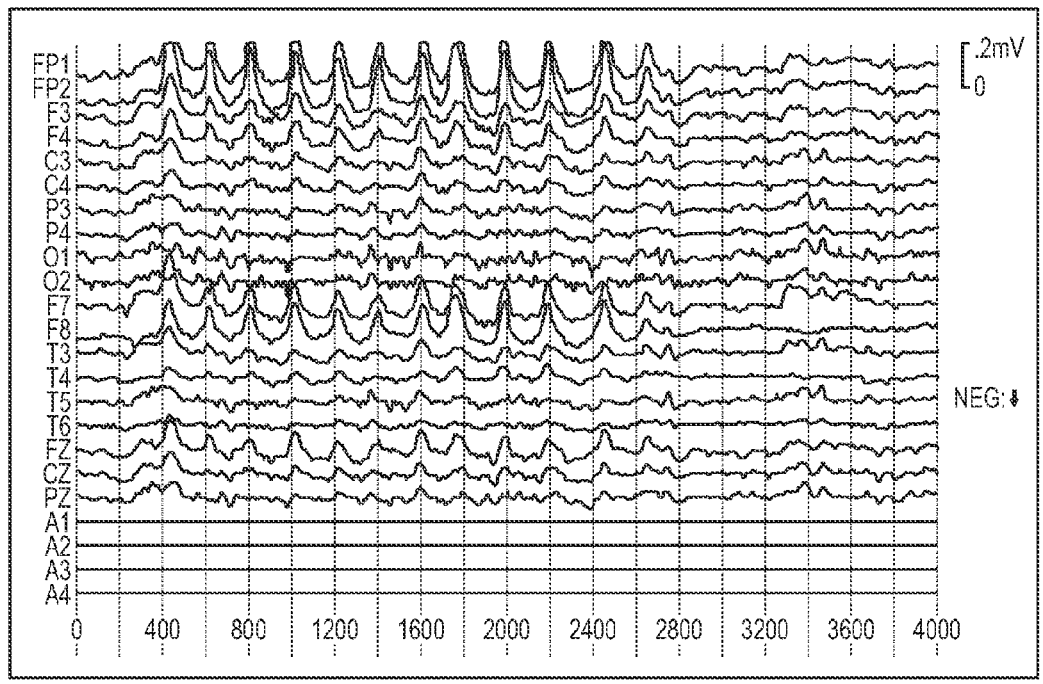

FIGS. 17A and 17B illustrate an example of EEG data that may be gathered during an EEG test in accordance with embodiments of the present invention. The raw EEG data in FIG. 17A represent an example of "good" eyes-closed data. The raw EEG data in FIG. 17B represent an example of "bad" EEG data due to the inclusion of an eye blink artifact.

According to various embodiments, the EEG data can be analyzed in terms of the amount of EEG wave activity in discrete frequency bands. The following list gives one example of discrete frequency bands that may be used in analyzing the EEG data:

Delta refers to any frequency up to 4 Hz.
Theta refers to any frequency from 4 to 8 Hz.
Alpha refers to any frequency from 8 to 13 Hz.
Beta refers to any frequency from 13 to 36 Hz.
Gamma refers to any frequency greater than 36 Hz.

According to various embodiments, EEG assessments can be performed on individuals in the following states: eyes-closed resting, eyes-open resting, eyes-closed active, and eyes-open active. Delta, theta, alpha, beta, and gamma waves can be measured in all four states. Delta waves, the lowest frequency, are the dominant frequency in lethargic individuals. Theta waves, so-called slow-activity waves, are increased during distracted and unfocused behavior. Alpha waves correlate with a relaxed state and are believed to promote mental resourcefulness. Beta waves, so-called fast activity waves, are the dominant frequency in alert individuals and correlate with mental focus and mental activity. Gamma waves are associated with high-level information processing and increase during the performance of information-rich tasks.

In some embodiments, EEG data is collected when individuals are resting, with eyes closed. In addition to resting EEG, some embodiments provide for the collection of EEG activity elicited in response to external stimuli (e.g., a tone or flash of light). One such evoked response is the P300 component, so-called because it occurs approximately 300 milliseconds after the external stimulus. The P300 component appears to be correlated with the processing of new information and updating memory when attention is engaged. The P300 component is composed of two subcomponents, P3a and P3b. P3a amplitude correlates with frontal lobe activity, whereas P3b activity correlates with parietal area activity. P3a and P3b activity are quantified by measuring the amplitude (size) and latency (speed) of each event.

P300 latency is an index of stimulus processing and can be used as a motor-free measure of cognitive function. P300 latency has been found to negatively correlate with cognitive function in normal subjects. Shorter latencies, therefore, are associated with superior cognitive performance during neuropsychological tests of attention and memory. P300 assessment is a reasonably reliable method to analyze certain aspects of brain function, and P300 measurements have comparable variability to routine clinical assay variability (e.g., a blood screening panel).

FIG. 18 is a flow chart illustrating a set of operations 1510 for gathering EEG data in accordance with one or more embodiments of the present invention.

Figure 19:
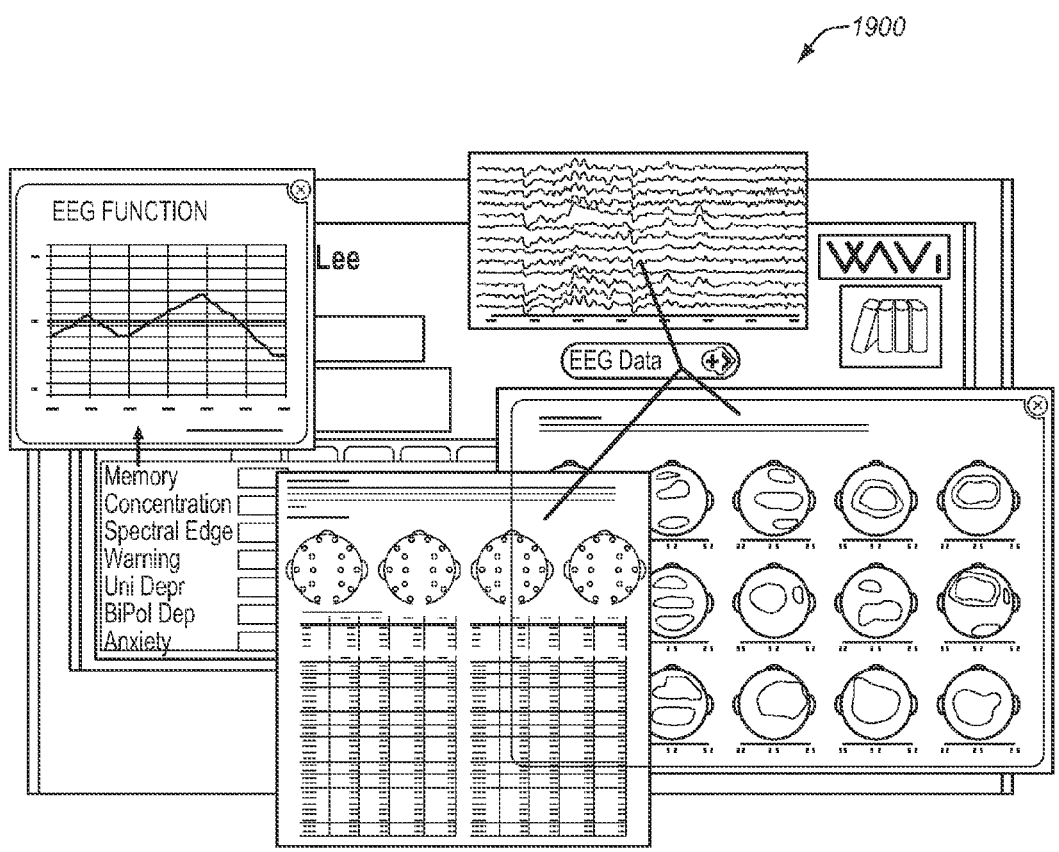
FIG. 19 is a screen shot 1900 of an example of a user interface that can be used to help a user interpret EEG data in accordance with various embodiments of the present invention.

FIG. 19 is a screen shot 1900 of an example of a user interface that can be used to help a user interpret EEG data in accordance with various embodiments of the present invention. As illustrated in FIG. 19, the EEG data can be presented in different formats as selected by the user. In addition, various scales for conditions that are being monitored (e.g., BiPolar, Anxiety, Pre-Dementia, etc.) by the application interface which has been set up by the user are listed.

Figure 20A:
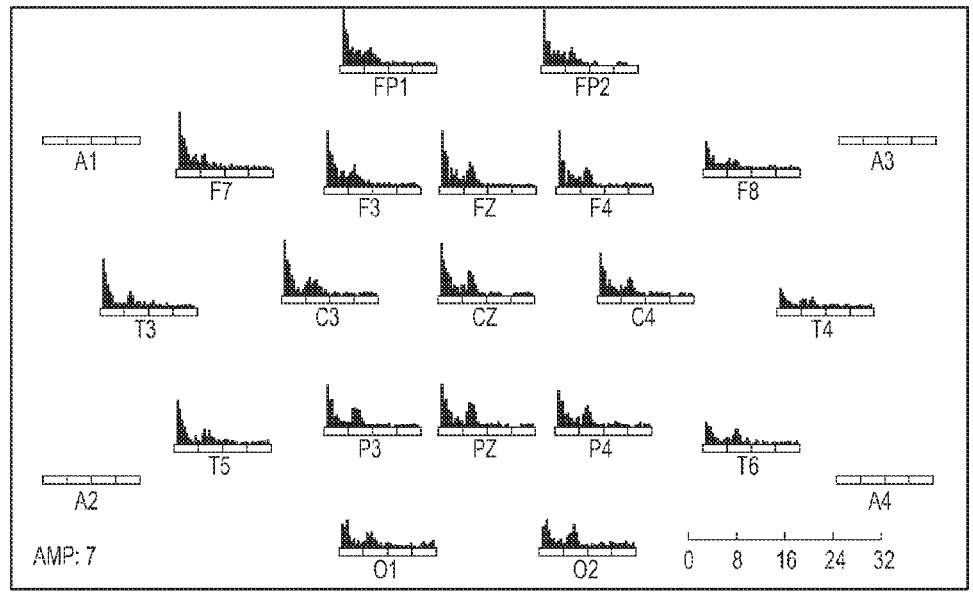
FIG. 20A is a screen shot of EEG data presented in a spectral array that may be presented in accordance with some embodiments of the present invention.

FIG. 20A is a screen shot of EEG data presented in a spectral array that may be presented in accordance with some embodiments of the present invention. To generate the spectral array shown in FIG. 20A, the raw EEG waves for each electrode are transformed into magnitude or power spectrums. From this type of display, a trained clinician could derive the distribution of power and amplitude (strength) of the brainwaves at each site.

Figure 20B:
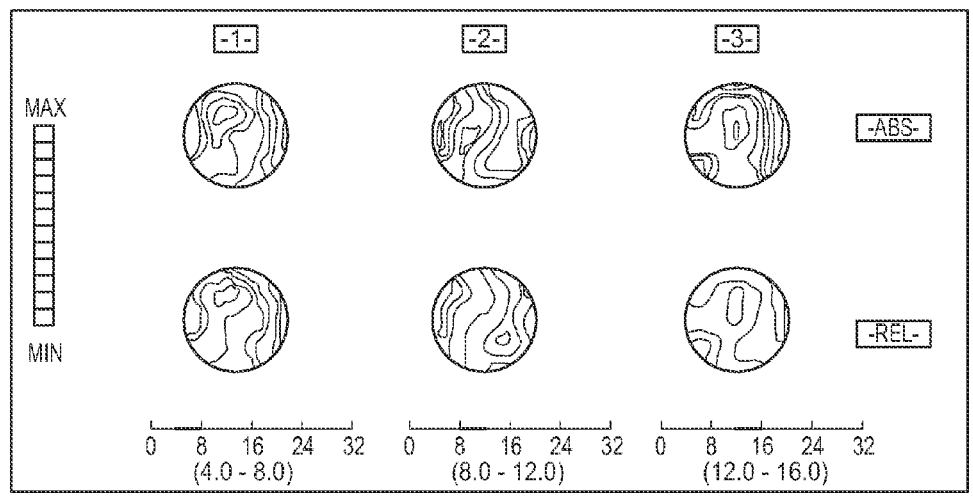
FIG. 20B is a screen shot of topographic maps of the raw EEG data that may be presented in accordance with one or more embodiments of the present invention.

FIG. 20B is a screen shot of topographic maps of the raw EEG data that may be presented in accordance with one or more embodiments of the present invention. As illustrated in FIG. 20B, the topographic maps summarize EEG data by representing power values (i.e., voltage variations) in selected frequencies at selected electrode sites.

Figure 21A:
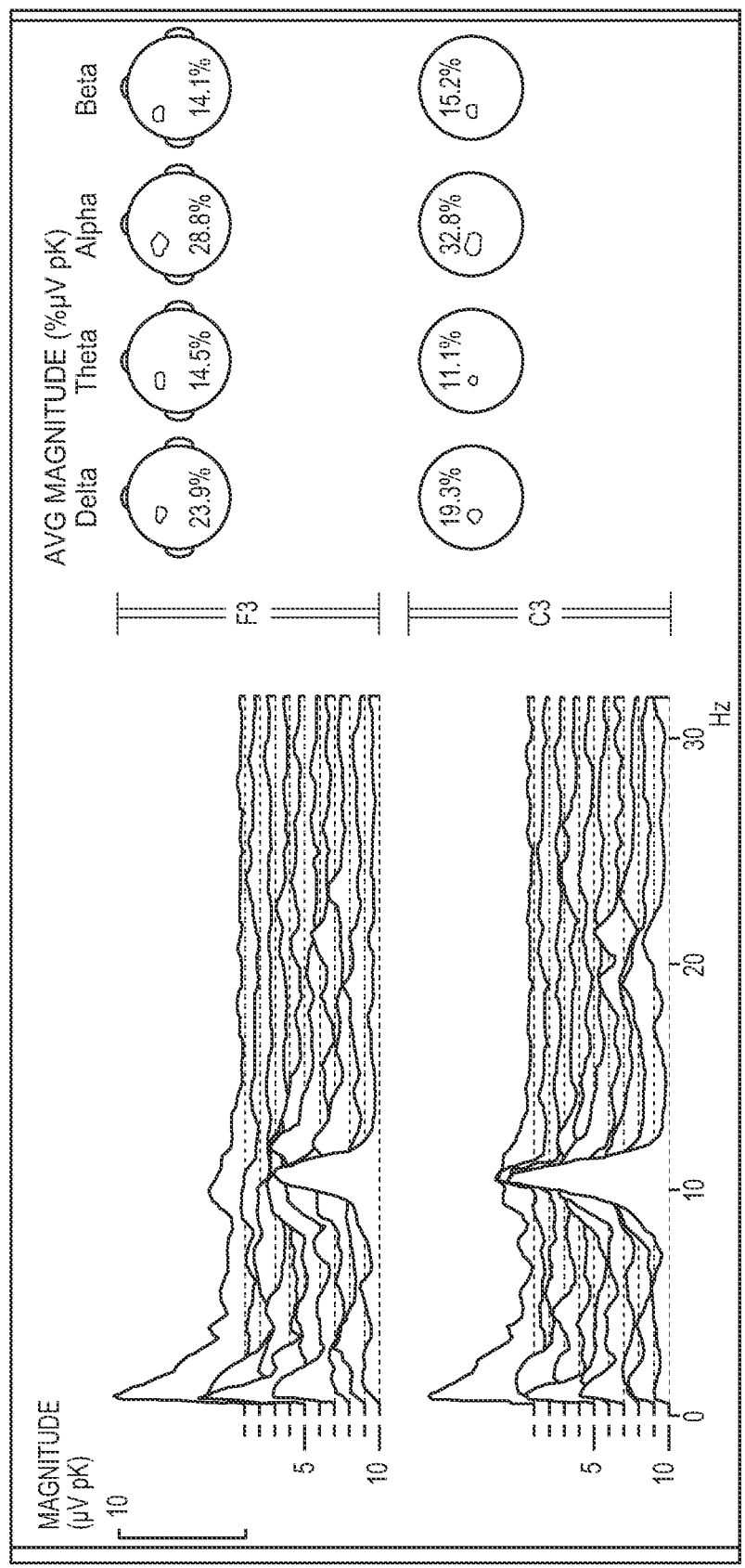
FIG. 21A illustrates a screen shot showing a compressed spectral array of raw EEG data that may be presented in accordance with embodiments of the present invention.

FIG. 21A illustrates a screen shot showing a compressed spectral array of raw EEG data that may be presented in accordance with embodiments of the present invention. The compressed spectral array illustrates how the spectrum of EEG evolves over time and can be useful for demonstrating certain trends in the data over time which are not observable in many of the other display formats.

Figure 21B:
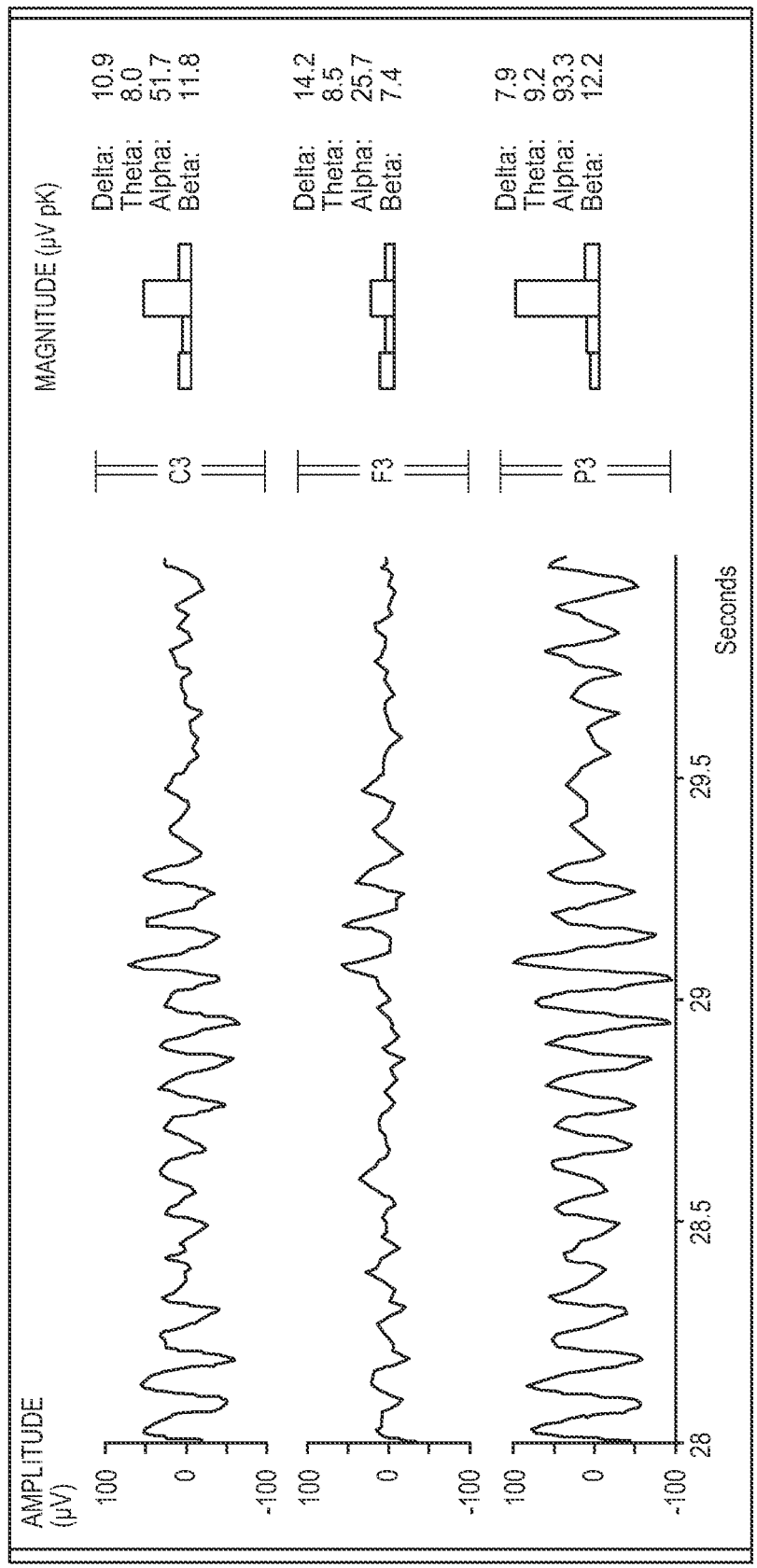
FIG. 21B illustrates a screen shot of a trend analysis of the raw EEG data that may be presented in accordance with various embodiments of the present invention.

FIG. 21B illustrates a screen shot of a trend analysis of the raw EEG data that may be presented in accordance with various embodiments of the present invention. According to various embodiments, trend analysis of the raw EEG data display are used to display the fluctuations of individual frequency bands over time.

Figure 22:
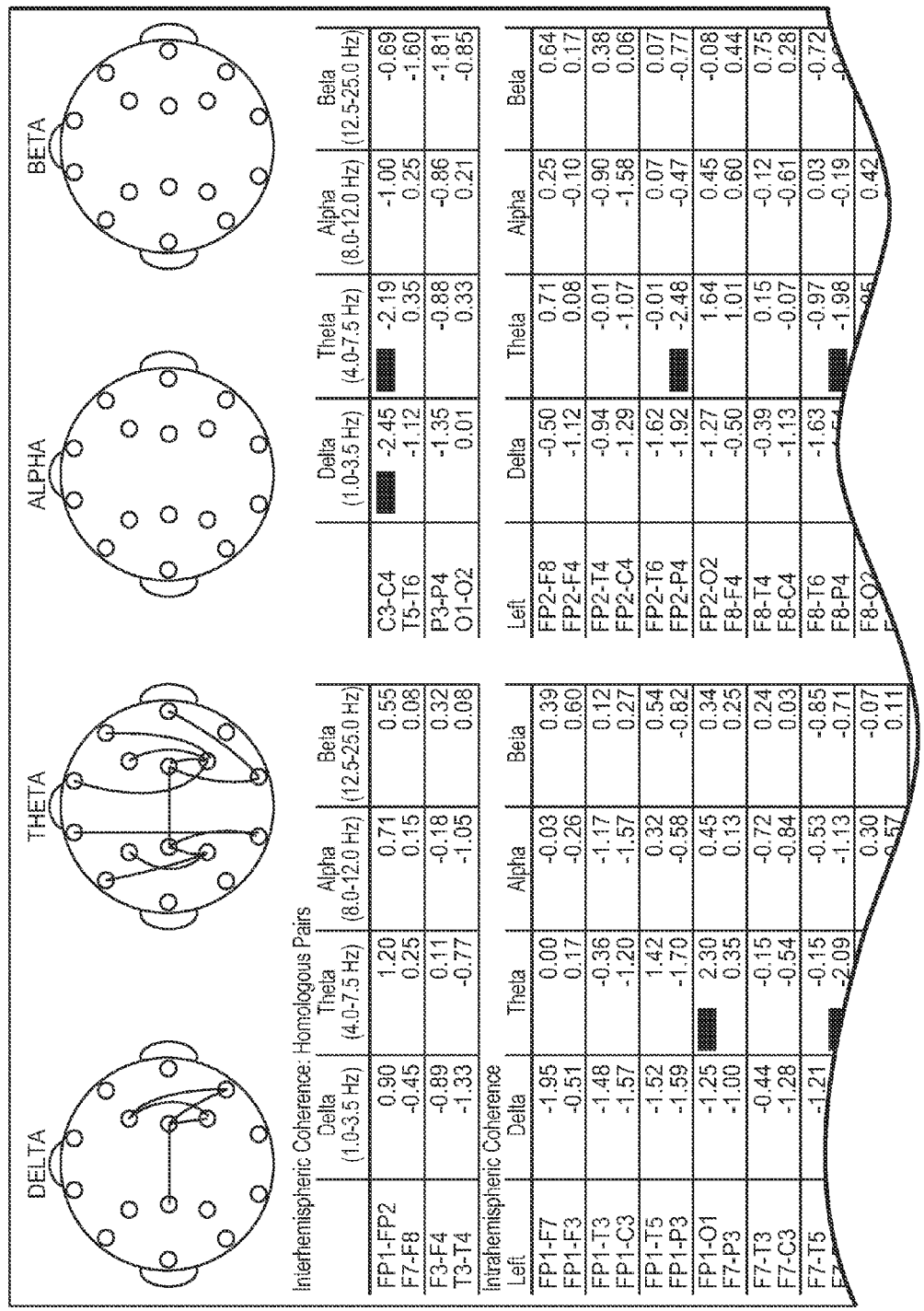
FIG. 22 is an example of a normative reference database comparison using coherence z-scores that may be generated in accordance with one or more embodiments of the present invention.

FIG. 22 is an example of a normative reference database comparison using coherence z-scores that may be generated in accordance with one or more embodiments of the present invention. The normative reference database comparison shown in FIG. 22 is a frequency-contingent cross correlation measure indexing the amount of shared activity between two scalp regions. This report is produced, according to some embodiments, by looking for clinician variations from normal EEG data from people with similar demographics (e.g., same age group) as the test subject.

Figure 23:
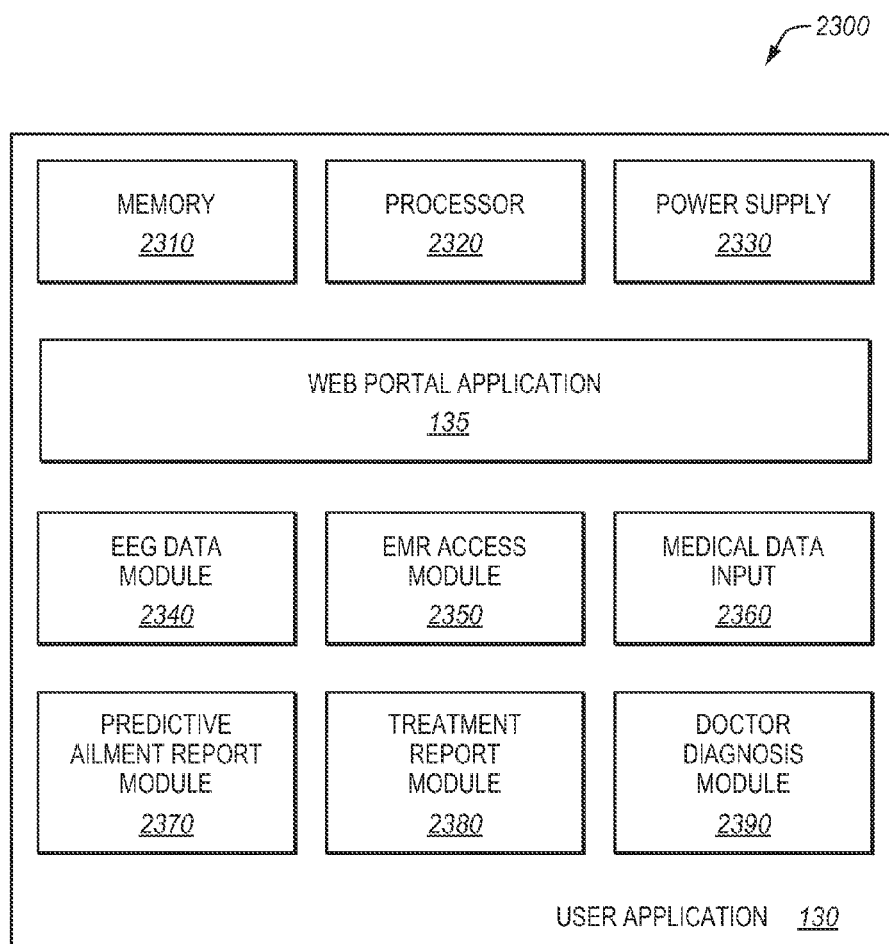
FIG. 23 is block diagram illustrating various components that may be present in a user application 130 in some embodiments of the present invention.

FIG. 23 is block diagram illustrating various components that may be present in a user application 130 in some embodiments of the present invention. The embodiments of user application 130 illustrated in FIG. 23 include the hardware components allowing user application 130 to be sold as a contained system. In other embodiments, user application 130 does not include a power supply, memory store, and/or processor. Some of these embodiments could be implemented by a user using a computer system as described elsewhere in the application.

The embodiments of user application 130 shown in FIG. 23 include the following components, modules, and applications: web portal application 135, a memory store 2310, a processor 2320, power supply 2330, EEG data module 2340, EMR access module 2350, medical data input module 2360, predicative ailment report module 2370, treatment report module 2380, and doctor diagnosis module 2390. Other embodiments of the present invention may include some, all, or none of these components, modules, and/or applications along with other modules, applications, or components. Still yet, various embodiments may incorporate two or more of these modules, applications, and/or components into a single module or application. Some embodiments associate a portion of the functionality of one or more of these modules with a different module. For example, in various embodiments, the various "report" modules (e.g., 2370 and 2380) can collectively be considered part of a report module.

According to various embodiments of the present invention, memory store 2310 can be a local memory store such as random access memory, a hard drive, or the like. Similarly, in some embodiments, memory store 2310 can be a remote data storage device such as an off-site database. Memory store 2310 can store data (e.g., EEG data, medical data, etc.) temporarily or permanently. In some cases, memory store 2310 includes computer executable code which can be run on processor(s) 2320. For example, in some embodiments, the computer executable code stored in memory store 2310 is designed for executing the functionality of the one or more modules and/or applications associated with user application 130. Still yet, in some embodiments, memory store 2310 has stored thereon one or more local versions of a normative database, a correlative database, a patient EEG database, and a data mining database.

According to various embodiments, web-portal application 135 may be used by user application 130 to connect to remote analysis platform 150 through network 140. As previously described, a variety of information can be transferred between the remote analysis platform 150 and user application 130. For example, EEG data, data relations, medical data, and the like can be transferred, according to some embodiments, from user application 130 to analysis platform 150. Similarly, various reports, statistical characterization results, and the like may be transferred back from analysis platform 150 to user application 130. In some embodiments, web portal application 135 is able to encrypt and decrypt the information that is being sent and received. Some embodiments of user application 130 include a communications module (not shown in FIG. 23) configured to securely transmit the one or more sets of EEG data relating to the test subject to remote analysis platform 150.

In some embodiments, user application 130 is a web-based Internet appliance running on analysis platform 150. The web-based Internet application can be accessed over network 140 either through a web-browser or through a custom computer application.

EEG data module 2340, according to one embodiment, provides an interface between the data acquisition and display module 120 and user application 130. EEG data module 2340 translates any requests for more EEG data from the user application 130 into a format required by the destination component. Similarly, module 2340 is able to translate and/or direct incoming requests and/or data to the appropriate module or application within the user application 130. In some embodiments, EEG data module 2340 is a receiving module that is configured to receive one or more sets of EEG data relating to a test subject (e.g., in real-time or as a batch process) and store the one or more sets of EEG data in a patient EEG database.

Once EEG data is received through EEG data module 2340, the data may be associated with one or more sets of data received through EMR access module 2350. EMR access module 2350, according to one embodiment, provides an interface between the EMR databases (e.g., 125a and 125b) and user application 130. EMR access module 2350 translates any requests for electronic medical records from the user application 130 into a format required by the destination component. Similarly, module 2350 is able to translate and/or direct incoming requests (e.g., requests for passwords or other authentication) and/or data to the appropriate module or application within the user application 130.

In some embodiments, a person using user application 130 may select one or more preferences about the data being presented. For example, a doctor may prefer to see various components of EMR data received or to see the EEG presented in a certain format (e.g., raw data, trend analysis, etc.). In addition, the doctor may want to enter additional information which is missing from the EMR or is based on a current assessment of the patient. To this end, some embodiments use medical data input module 2360 to present user interface screens for the entry of medical data and comments/notes from the doctor. In one embodiment, medical data input module 2360 automatically translates the medical information entered by the doctor in the CPT codes. In some cases, there are a series of dialog boxes, menus, radio buttons, and the like that allow for the doctor to input information such as treatment plans, diagnoses, and the like.

Predictive ailment report module 2370 and treatment report module 2380 are available in some embodiments of the present invention. In accordance with various embodiments, these modules are able to interface with the EMRs of the patient, storage databases, and/or analysis platform 150 to request information about current and past treatments and previously generated predictive ailment reports. Modules 2370 and 2380 prepare the reports to be presented in one or more display formats.

In one or more embodiments, doctor diagnosis module 2390 can generate user interface screen(s) that allow the doctor to input a diagnosis. In some embodiments, module 2390 provides for the entry of a diagnosis through one or more menus, dialog boxes, radio button selections, and the like. In some cases, diagnosis module 2390 can interface with the analysis platform 150 to generate a short list of diagnoses for the doctor to choose from based on the results of the statistical characterization of the EEG data. If the doctor likes one of those diagnoses, he can select it. If not, the doctor is able to enter a different diagnosis through the user interface screen options.

Figure 24:
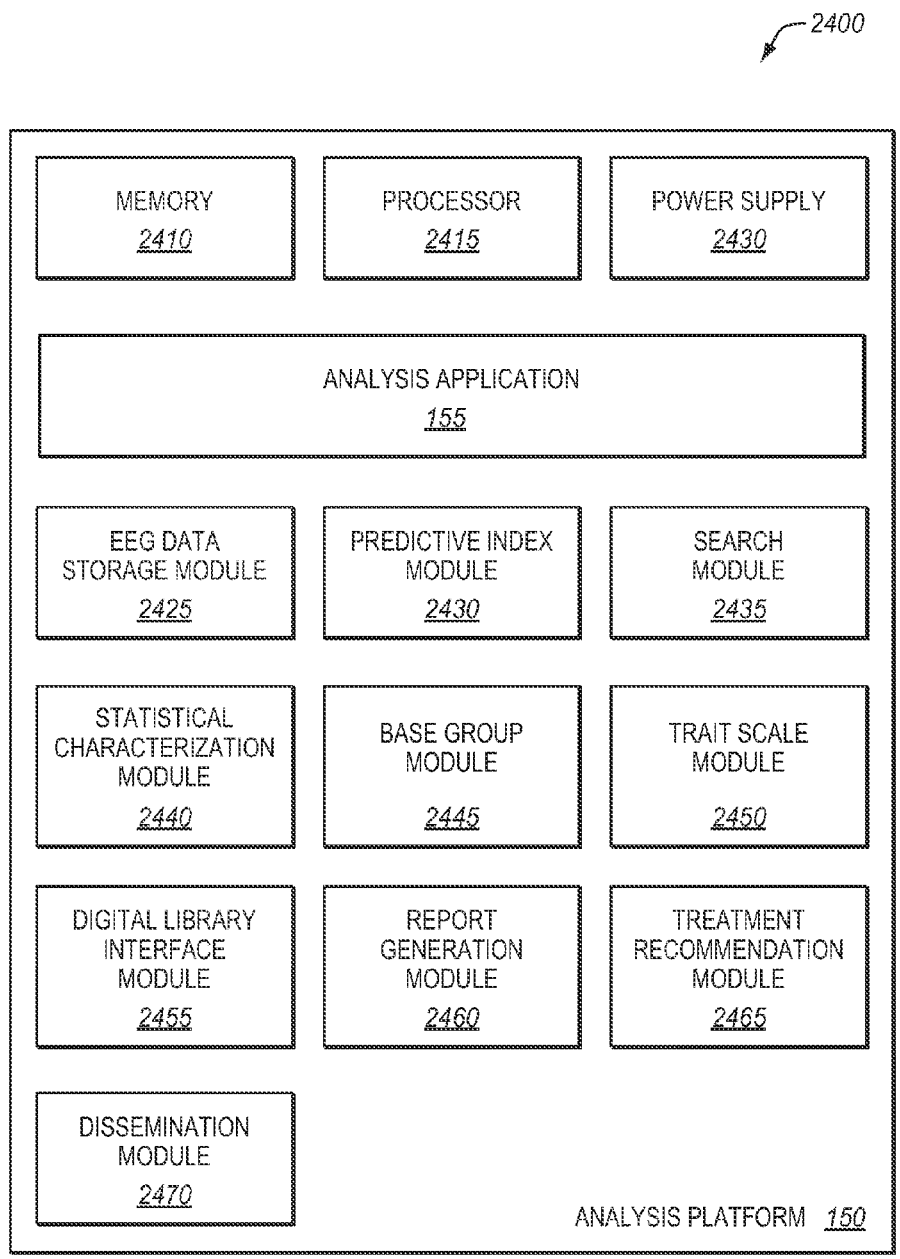
FIG. 24 is a block diagram illustrating various components that may be present in analysis platform 150 in accordance with some embodiments of the present invention.

FIG. 24 is a block diagram illustrating various components that may be present in analysis platform 150 in accordance with some embodiments of the present invention. The embodiments of analysis platform 150 illustrated in FIG. 24 include the hardware components allowing analysis platform 150 to be sold as a self-contained system. In other embodiments, analysis platform 150 does not include a power supply, memory store, and/or processor. These embodiments take advantage of additional hardware from the user such as a computer system as described elsewhere in the application.

The embodiments of analysis platform 150 shown in FIG. 24 include the following components, modules, and applications: analysis application 145, a memory store 2410, a processor 2415, power supply 2420, EEG data storage module 2425, predictive index module 2430, search module 2435, statistical characterization module 2440, base group module 2445, trait scale module 2450, digital library interface module 2455, report generation module 2460, treatment recommendation module 2465, and dissemination module 2470. Other embodiments of the present invention may include some, all, or none of these components, modules, and/or applications along with other modules, applications, and/or components. Still yet, various embodiments may incorporate two or more of these modules, applications, and/or components into a single module and/or associate a portion of the functionality of one or more of these modules with a different module.

According to various embodiments of the present invention, memory store 2410 can be a local memory store such as a random access memory, a hard drive, or the like. Similarly, in some embodiments, memory store 2310 can be a remote data storage device such as an off-site database. In some cases, memory store 2310 includes computer executable code which can be run on processor(s) 2415. For example, in some embodiments, the computer executable code stored in memory store 2415 is designed for executing the functionality of the one or more modules and/or applications associated with analysis application 155. Still yet, in some embodiments, memory store 2415 has stored thereon a normative database 160, a correlative database 165, a patient EEG database, and a data mining database 170.

EEG data storage module 2425 is configured to store the acquired EEG data received through the web-based Internet appliance in a patient EEG database. In some embodiments, module 2425 is able to store additional medical information and data relations. Using demographic information received from user application 130, base group module 2445 is able to search the normative database and select distributions of normal patient data that correspond to the demographics of the test subject. In some cases, the doctor is able to set the selection criteria through user application 130. In other cases, default search rules are pre-set within base group module 2445 either by the doctor or system designers.

Once EEG data, desired data relations, and the base group are received, statistical characterization module 2440 calculates normative variations of the test subject EEG data with EEG data of a base group selected from data in the normative database 160. In some embodiments of the present invention, statistical characterization module 2440 is associated with the remote analysis platform. In other embodiments, statistical characterization module 2440 is associated with user application 130. In this case, the selection of normal data and distributions from normal database 160 can be transferred back through network 140 to user application 130. In some cases, local versions of the normal database are associated with user application 130.

Once the statistical characterization of the test subject's EEG data is completed, the results are communicated to report generation module 2460. Module 2460 can be used to generate one or more reports such as a treatment report, a predictive ailment report, and others. According to various embodiments, to generate a treatment report, treatment index 230 could be accessed and treatments associated with the results retrieved. In some embodiments, treatment recommendation module 2465 is used to automatically associate the normative variations of the test subject EEG data with one or more ailments. To this end, treatment recommendation module 2465 could be used to search informational vehicles in the digital library for treatment plans relating to the statistical characterization results. As another example, a treatment report could be generated based on keywords in the doctor's diagnosis entered though diagnostic module 2390 in user application 130.

In some embodiments, predictive index module 2430 is configured to access the electronic medical records of the patient and build predictive indexes based on the acquired EEG data and information in the electronic medical records.

Search module 2435, according to various embodiments, is able to receive requests to search the digital library for articles relating to a particular ailment or condition. Search module 2435 translates the request into the appropriate format and uses digital library interface module 2455 to search the digital library for information vehicles relating to a particular ailment or condition. In addition to searching for information vehicles in the digital library, search module 2435 also can process the request and use trait scale module 2450 to search for data relations that have been correlated with the condition or ailment of interest.

Figure 25:
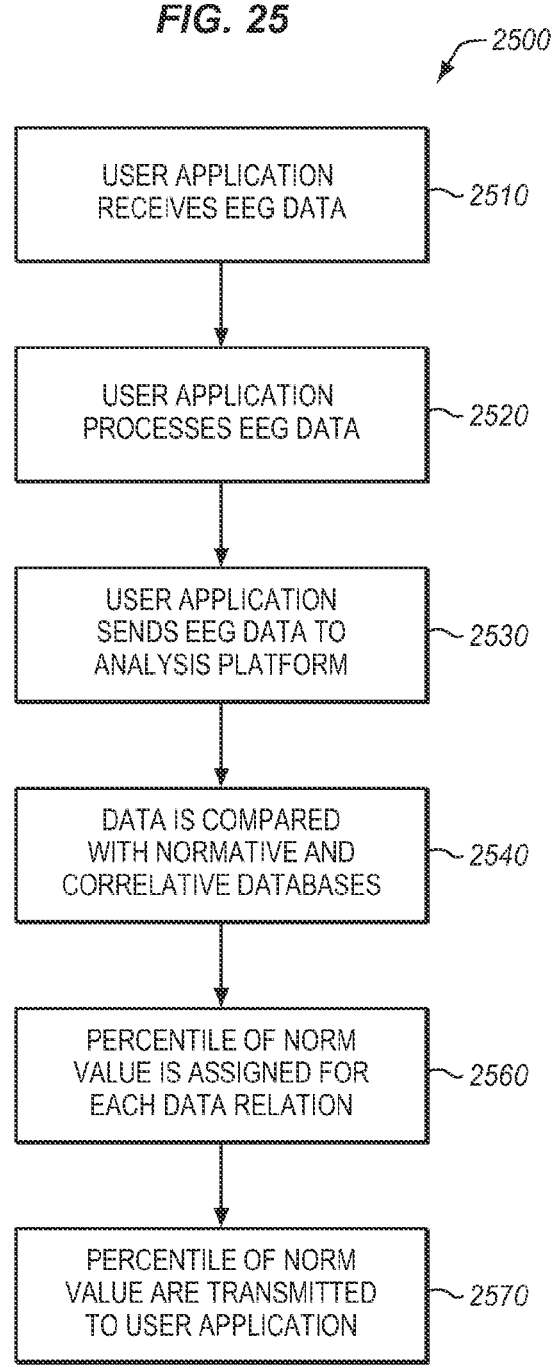
FIG. 25 is a flow chart with a set of operations 2500 for generating a statistical analysis in accordance with embodiments of the present invention.

FIG. 25 is a flow chart with a set of operations 2500 for generating a statistical analysis in accordance with embodiments of the present invention. Patient EEG data is received from a patient using a wireless helmet-like transducer during receiving operation 2510. In various embodiments, user application 130 can process the received EEG data using processing operation 2520. According to various embodiments, processing operation 2520 is able to verify that the received EEG data is of good quality and sufficient length for statistical characterization. In some embodiments, processing operation 2520 computes one or more EEG parameters and/or data relation as requested for analysis by the user.

Sending operation 2530 transfers the EEG data from the user application to the analysis platform. In some cases, additional information such as patient medical data, data relation formulas, and the like also can be transmitted during sending operation 2530. In one or more embodiments, additional information can be accessed through electronic medical records (EMRs) of the patient. This additional information can be used to determine patient characteristics for determining/selecting the base group for the statistical analysis. In addition, in some embodiments, information can be received from a patient's psychological questionnaire that can be used in determining the base group used in the statistical characterization.

The EEG data is statistically characterized (e.g., by calculating normative variations of the patient EEG data with EEG data of a base group) during comparison operation 2540. Assignment operation 2560 assigns a percentile of normal values for each requested data relation. These assigned percentiles then are transmitted back to the user application 130 with transfer operation 2570.

According to some embodiments, access to articles in a digital library based on the statistical characterization of the patient EEG data can also be provided to the user. The articles, in accordance with various embodiments, may suggest one or more possible interpretations of the statistical characterization of the patient EEG data.

Figure 26:
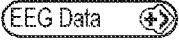
FIG. 26 is a screen shot of an example user interface 2600 that may be used in accordance with various embodiments of the present invention.
Figure 27A:
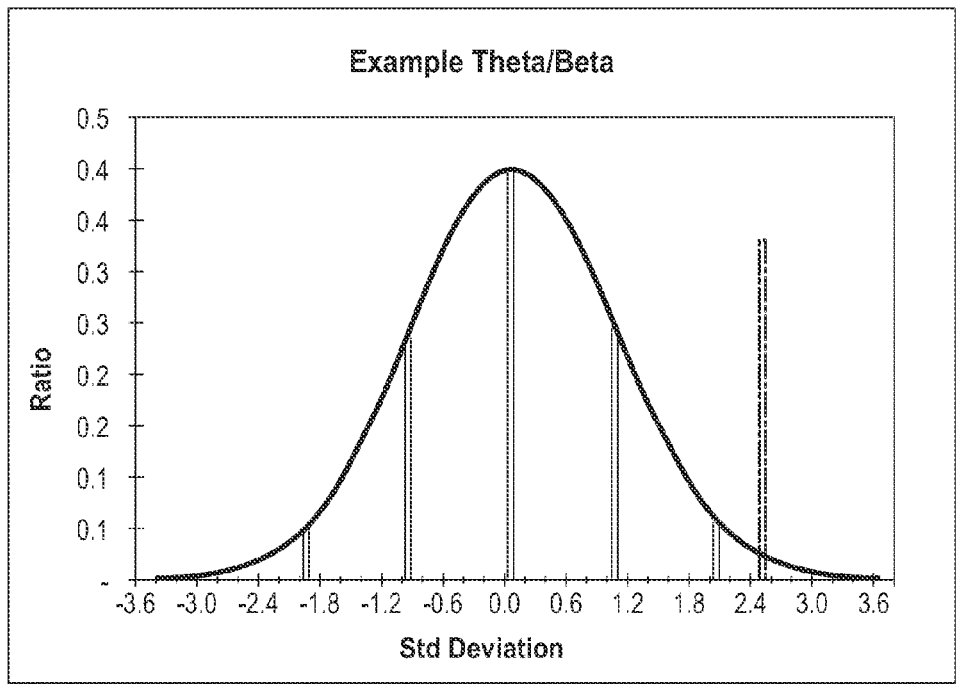
FIGS. 27A and 27B are examples of how a data relation of a patient's EEG data may fall within the distribution of normal EEG data in accordance with one or more embodiments of the present invention.
Figure 27B:
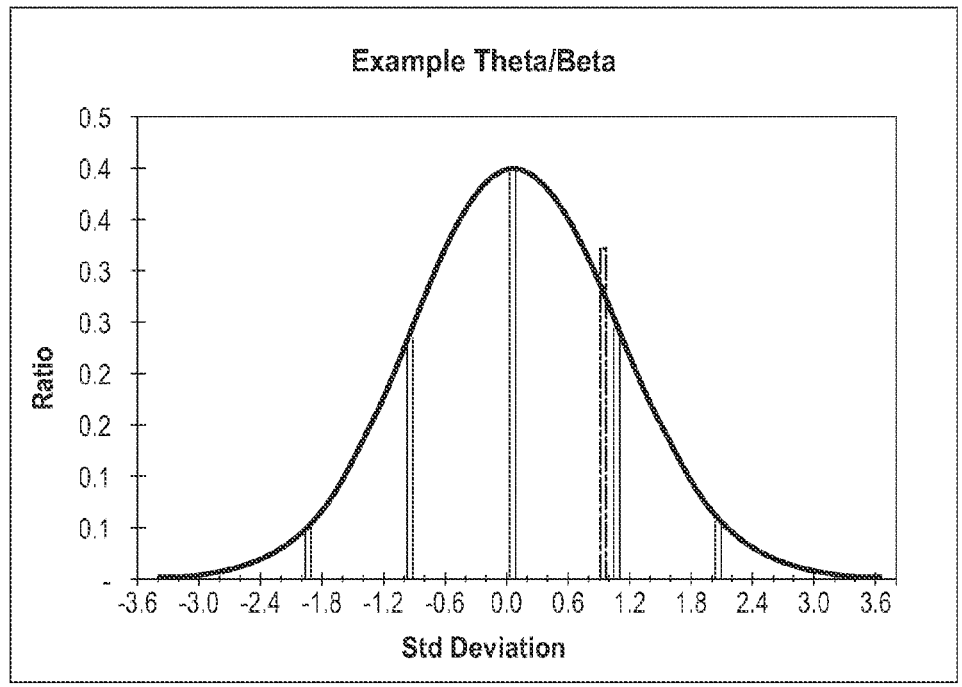

FIG. 26 is a screen shot of an example user interface 2600 that may be used in accordance with various embodiments of the present invention;

FIGS. 27A and 27B are examples of how a data relation of a patient's EEG data may fall within the distribution of normal EEG data in accordance with one or more embodiments of the present invention, FIG. 28 is a flow chart with an example of a set of operations 2800 to update a predictive index 240 in accordance with some embodiments of the present invention.

Figure 29:
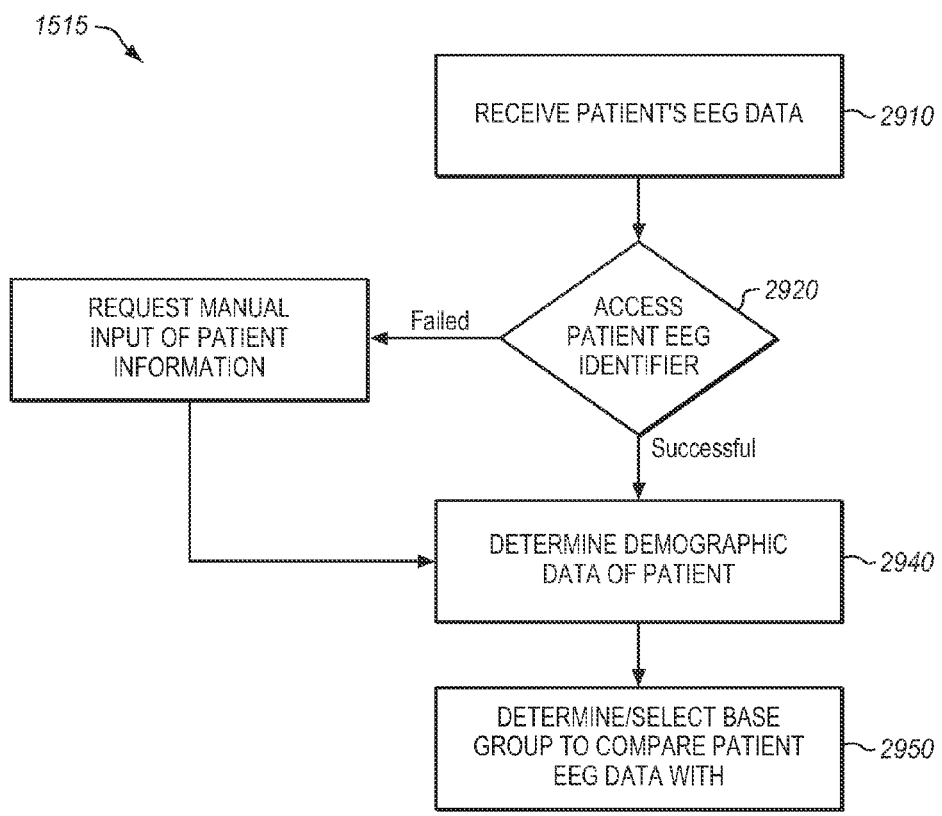
FIG. 29 is a flow chart with an example of a set of operations 1515 to determine a base group in accordance with embodiments of the present invention.

FIG. 29 is a flow chart with an example of a set of operations 1515 to determine a base group in accordance with embodiments of the present invention.

Figure 30:
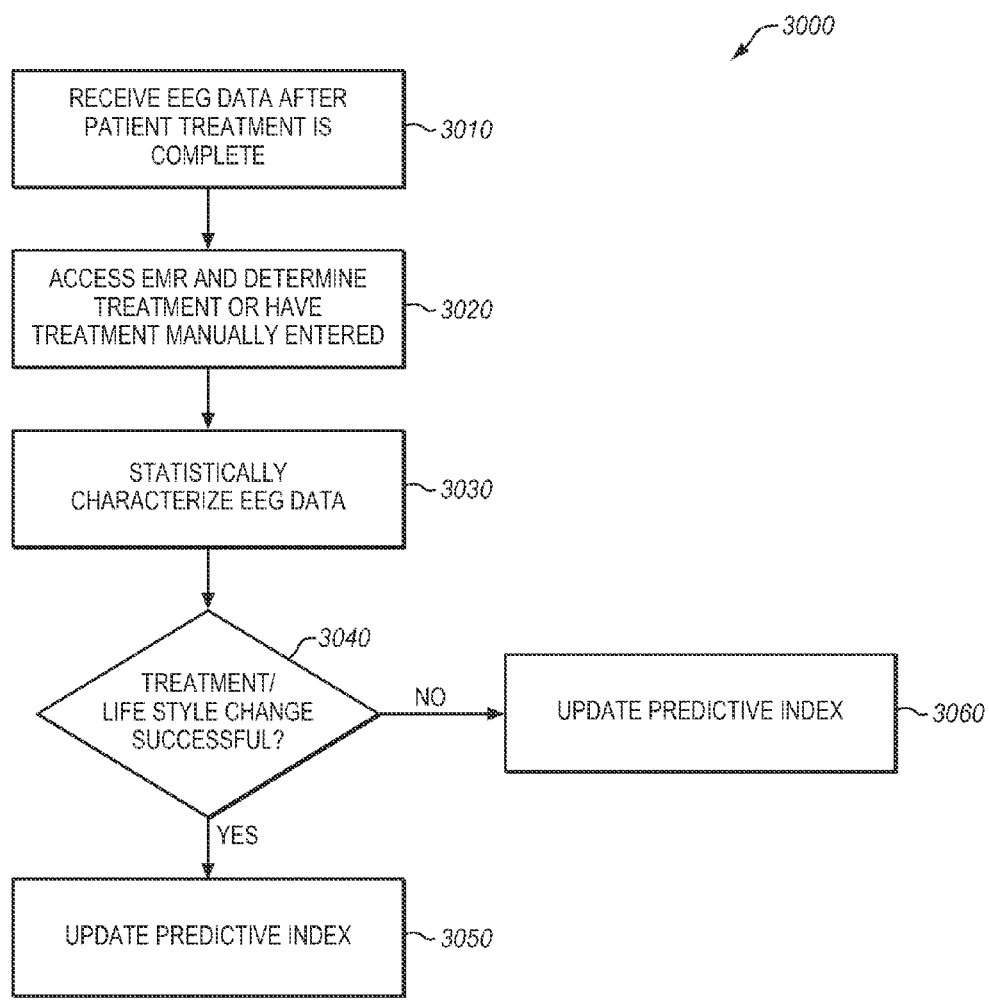
FIG. 30 is a flow chart with an example of a set of operations 3000 to update a predictive index in accordance with one or more embodiments of the present invention.

FIG. 30 is a flow chart with an example of a set of operations 3000 to update a predictive index in accordance with one or more embodiments of the present invention.

Various modifications and additions can be made to the embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations and all equivalents thereof.

What is claimed as new and desired to be protected by Letters Patent of the United States is:

1. A medical data analysis system for providing a physician with access to medical information sources which correlate to anomalies identified in patient-specific medical data, comprising:
 a physician terminal device for providing a physician with a user interface;
 a memory for storing at least one set of patient-specific medical data relating to an identified patient, which patient medical data comprises a plurality of measurements of biomarkers that correspond to a biological property of one or more organisms in the patient;
 a server, communicatively connected to the physician terminal device, comprising:
  a digital library for providing access to a plurality of information sources which relate to interpreting patient medical data and diseases associated with the patient medical data; and
  a control database which contains a plurality of sets of ailment-specific biomarkers, each of which correspond to a set of characteristic biological properties that can be detected and measured in a patient, and each of which are indicative that an organism is afflicted with a predetermined ailment;
 a physician application, executing on the physician terminal device, for enabling the physician to select a plurality of sets of ailment-specific biomarkers via the physician terminal device;
 wherein the server further comprises:
  a data characterization module for calculating, using the physician selected sets of ailment-specific biomarkers, normative variations in the patient-specific medical data, when compared to the sets of ailment-specific biomarkers, to identify anomalies in the patient-specific medical data;
  a digital library interface module, responsive to receipt of the patient-specific medical data collected from and about the identified patient and identified anomalies calculated by the data characterization module, for automatically searching the digital library to identify information sources relating to interpretations of the identified patient medical data of the identified patient that correlates with each of the biomarkers in each of the selected sets of ailment specific biomarkers to enable the physician to identify at least one possible ailment associated with the patient medical data; and
  an information access module for providing the physician with access to the information sources identified by the digital library interface module.

2. The medical data analysis system of claim 1, further comprising:
a secure memory for storing patient-specific medical data collected from and about an identified patient for use by the physician.

3. The medical data analysis system of claim 1 wherein the patient-specific medical data comprises:
monitoring data collected from one or more medical devices operable to measure physiological data relating to the identified patient.

4. The medical data analysis system of claim 1 wherein the digital library comprises:
a plurality of publication information each of which relates to interpreting medical data and possible diseases associated with the medical data.

5. The medical data analysis system of claim 1 wherein the data characterization module comprises:
a statistical analyzer for comparing the patient-specific medical data to demographic-matched reference normative data.

6. The medical data analysis system of claim 5 wherein the data characterization module further comprises:
an ailment identifier for generating data which identifies at least one possible disease that corresponds to a variation of the patient-specific medical data from the demographic-matched reference normative data.

7. The medical data analysis system of claim 6 wherein the data characterization module further comprises:
an ailment correlator for identifying information sources relating to the at least one possible disease associated with the patient medical data.

8. The medical data analysis system of claim 5 wherein the data characterization module further comprises:
an ailment filter, responsive to data received from the physician indicative of at least one known disease, for activating the statistical analyzer to select demographic-matched reference normative data relating to the at least one known disease.

9. The medical data analysis system of claim 5 wherein the data characterization module comprises:
a predictive analyzer, responsive to the patient-specific medical data, for using at least one of correlative databases, predictive databases, and trait indices, to generate an estimation of a likelihood that the identified patient will develop one or more particular diseases.

10. The medical data analysis system of claim 9 wherein the digital library interface module comprises:
an ailment correlator, responsive to the predictive analyzer generating an estimation of a likelihood that the identified patient will develop one or more particular diseases, for identifying information sources relating to the one or more particular diseases.

11. The medical data analysis system of claim 1 wherein the information access module comprises:
a security module for authenticating an identity of the physician; and
an authorization module for determining that the authenticated physician has authorization to access any of the patient-specific medical data and the information sources relating to the patient.

12. A method of operating a medical data analysis system for providing a physician with access to medical information sources which correlate to anomalies identified in patient-specific medical data relating to an identified patient, comprising:
storing in a memory at least one set of patient-specific medical data relating to an identified patient, which patient medical data comprises a plurality of measurements of biomarkers that correspond to a biological property of one or more organisms in the patient;
providing access to a digital library, resident on a server, which contains a plurality of information sources which relate to interpreting patient-specific medical data and possible diseases associated with the patient medical data;
executing a physician application on a physician terminal device to provide the physician with access to a control database which contains medical data indicative of measurements taken on control subjects;
enabling the physician to select a plurality of sets of ailment-specific biomarkers via the physician terminal device;
identifying patient medical data of the identified patient that correlates with each of the biomarkers in each of the selected sets of ailment-specific biomarkers;
calculating, using the physician selected sets of ailment-specific biomarkers, normative variations in the patient-specific medical data, when compared to the sets of ailment-specific biomarkers, to identify anomalies in the patient-specific medical data;
providing a digital library interface, in response to receipt of the patient-specific medical data relating to the identified patient collected from and about the identified patient and identified anomalies calculated by the step of calculating normative variations, for automatically searching the digital library to identify information sources relating to interpretations of the identified patient medical data of the identified patient that correlates with each of the biomarkers in each of the selected sets of ailment-specific biomarkers to enable the physician to identify at least one possible disease associated with the patient medical data using the interpretations of the identified anomalies; and
providing information access to the physician with access to the information sources identified by the digital library interface module.

13. The method of operating a medical data analysis system of claim 12, further comprising:
storing in a secure memory patient-specific medical data collected from and about an identified patient for use by the physician.

14. The method of operating a medical data analysis system of claim 12 wherein the patient medical data comprises:
monitoring data collected from one or more medical devices operable to measure physiological data relating the identified patient.

15. The method of operating a medical data analysis system of claim 12 wherein the step of providing access to digital library comprises:
electronically storing a plurality of publication information, each of which relates to interpreting medical data and possible diseases associated with medical data.

16. The method of operating a medical data analysis system of claim 12 wherein the step of calculating normative variations comprises:
comparing, via a statistical analyzer, the patient-specific medical data to demographic-matched reference normative data.

17. The method of operating a medical data analysis system of claim 16 wherein the step of calculating normative variations further comprises:

generating data which identifies at least one possible disease that corresponds to a variation of the patient data from the demographic-matched reference normative data.

18. The method of operating a medical data analysis system of claim 17 wherein the step of calculating normative variations further comprises:

identifying information sources relating to the at least one possible disease associated with the patient medical data.

19. The method of operating a medical data analysis system of claim 16 wherein the step of calculating normative variations further comprises:

activating, in response to data received from the physician indicative of at least one known disease, the statistical analyzer to select demographic-matched reference normative data relating to the at least one known disease.

20. The method of operating a medical data analysis system of claim 16 wherein the step of calculating normative variations comprises:

using, in response to the patient-specific medical data, at least one of correlative databases, predictive databases, and trait indices, to generate an estimation of a likelihood that the identified patient will develop one or more particular diseases.

21. The method of operating a medical data analysis system of claim 20 wherein the step of providing a digital library interface comprises:

identifying, in response to a predictive analyzer generating an estimation of a likelihood that the identified patient will develop one or more particular diseases, information sources relating to the one or more particular diseases.

22. The method of operating a medical data analysis system of claim 12 wherein the step of providing information access comprises:

authenticating an identity of the physician; and
determining that the authenticated physician has authorization to access any of the patient-specific medical data and the information sources relating to the patient.

* * * * *